(12) United States Patent
Wu et al.

(10) Patent No.: US 7,704,708 B2
(45) Date of Patent: Apr. 27, 2010

(54) MONOMERIC STREPTAVIDIN MUTEINS

(75) Inventors: Sau-Ching Wu, Calgary (CA); Sui-Lam Wong, Calgary (CA)

(73) Assignee: UTI Limited Partnership, Calgary (CA)

( * ) Notice: Subject to any disclaimer, the term of this patent is extended or adjusted under 35 U.S.C. 154(b) by 0 days.

(21) Appl. No.: 11/822,885

(22) Filed: Jul. 11, 2007

(65) Prior Publication Data

US 2008/0213801 A1 Sep. 4, 2008

Related U.S. Application Data

(62) Division of application No. 11/307,576, filed on Feb. 13, 2006, now Pat. No. 7,265,205.

(51) Int. Cl.
*C12P 21/06* (2006.01)
*C07K 1/00* (2006.01)

(52) U.S. Cl. ...................... 435/69.1; 530/350

(58) Field of Classification Search ................ 435/69.1; 530/350
See application file for complete search history.

(56) References Cited

U.S. PATENT DOCUMENTS

| | | | | |
|---|---|---|---|---|
| 5,672,691 | A | 9/1997 | Kopetzki et al. | ............ 530/413 |
| 5,973,124 | A | 10/1999 | Bayer et al. | ................. 530/402 |
| 6,022,951 | A | 2/2000 | Sano et al. | .................. 530/350 |
| 6,218,513 | B1 | 4/2001 | Anthony-Cahill et al. | ... 530/380 |
| 6,312,916 | B1 | 11/2001 | Kopetzki et al. | ............ 435/7.5 |

OTHER PUBLICATIONS

Argarana et al., "Molecular cloning and nucleotide sequence of the streptavidin gene," *Nucleic Acids Research*, 14:1871-1882, 1986.
Atwell et al., "Structural plasticity in a remodeled protein-protein interface," *Science Journal*, 278:1125-1128, 1997.
Bashir et al., "Adsorption of avidin on microfabricated surfaces for protein biochip applications," *Biotechnology and Bioengineering*, 73:324-328, 2001.
Bayer et al., "Application of avidin-biotin technology to affinity-based separations," *Journal of Chromatography*, 510:3-11, 1990.
Bayer et al., "Sodium dodecyl sulfate-polyacrylamide gel electrophoretic method for assessing the quaternary state and comparitive thermostability of avidin and streptavidin," *Electrophoresis*, 17:1319-1324, 1996.
Blake et al., "Structure of hen egg-white lysozyme," *Nature*, 206:757-761, 1965.
Dieckman et al., "High throughput methods for gene cloning and expression," *Protein Expression and Purification*, 25:1-7, 2002.
Ellison et al., "Limited proteolysis of native proteins: the interaction between avidin and proteinase K," *Protein Science*, 4:1337-1345, 1995.
Freitag et al., Structural studies of binding site tryptophan mutants in the high-affinity streptavidin-biotin complex, *J. Mol. Biol.*, 279:211-221, 1998.

Gallizia et al., Production of a soluble and functional recombinant streptavidin in *Escherichia coli*, *Protein Expression and Purification*, 14:192-196, 1998.
Gasteiger et al., "ExPASy: the proteomics server for in-depth protein knowledge and analysis," *Nucleic Acids Research*, 31:3784-3788, 2003.
Gill et al., "Calculation of protein extinction coefficients from amino acid sequence data," *Analytical Biochemistry*, 182:319-326, 1989.
Gonzalez et al., "Extremely high thermal stability of streptavidin and avidin upon biotin binding," *Biomolecular Engineering*, 16:67-72, 1999.
Guex et al., "Swiss-model and the Swiss PdbViewer: an environment for comparative protein modeling," *Electrophoresis*, 18:2714-2723, 1997.
Halling et al., "Zinc is associated with the subunit of DNA-dependent RNA polymeerase of *Bacillus subtilis*," *Biochemistry*, 16:2880-2884, 1997.
Hendrickson et al., "An avidin monomer affinity column for the purification of biotin-containing enzymes," *Analytical Biochemistry*, 94:366-370, 1979.
Hendrickson et al., "Crystal structure of core streptavidin determined from multiwavelength anomalous diffraction of synchrotron radiation," *Proc. Natl. Acad. Sci. USA*, 86:2190-2194, 1989.
Hunt et al., "From gene to protein: a review of new and enabling technologies for multi-parallel protein expression," *Protein Expression and Purification*, 40:1-22, 2005.
Hyre et al., "Ser45 plays an important role in managing both the equilibrium and transition state energetics of the streptavindin-biotin system," *Protein Science*, 9:878-885, 2000.
Jones et al., "Protein-protein interactions: a review of protein dimer structures," *Prog. Biophys. Molec. Biol.*, 63:31-65, 1995.
Laitinen et al., "Biotin induces tetramerization of a recombinant monomeric avidin," *The Journal of Biological Chemistry*, 276:8219-8224, 2001.
Laitinen et al., "Rational design of an active avidin monomer," *The Journal of Biological Chemistry*, 278:4040-4014, 2003.
Lesley et al., "High-throughput proteomics: protein expression and purification in the postgenomic world," *Protein Expression and Purification*, 22:159-164, 2003.
Lichty et al., "Comparision of affinity tags for protein purification," *Protein Expression & Purification*, 41:98-105, 2005.
Liu et al., "The univector plasmid-fusion system, a method for rapid construction of recombinant DNA without restriction enzymes," *Current Biology*, 8:1300-1309, 1998.
Livnah et al., "Three-dimensional structures of avidin and the avidin-biotin complex," *Proc. Natl. Acad. Sci. USA*, 90:5076-5080, 1993.

(Continued)

*Primary Examiner*—Maryam Monshipouri
(74) *Attorney, Agent, or Firm*—Fulbright & Jaworski

(57) ABSTRACT

The invention includes a streptavidin mutein having at least one mutation chosen to cause one or more of steric hindrance, charge repulsion, or improvement of solubility by changing interfacial hydrophobic residues to less hydrophobic or hydrophilic residues. The mutein may exist in monomeric form even in the presence of biotin, and reversibly binds to biotin. The invention also includes polynucleotides encoding such muteins, expression systems and host cells for producing such muteins. The invention also includes a method of capturing biotinylated molecules using the muteins of the invention.

17 Claims, 8 Drawing Sheets

OTHER PUBLICATIONS

Marttila et al., "Engineering of chicken avidin: a progressive series of reduced charge mutants," *FEBS Letters*, 441:313-317, 1998.

Marttila et al., "Recombinant NetraLite avidin: a non-glycosylated, acidic mutant of chicken avidin that exhibits high affinity for biotin and low non-specific binding properties," *FEBS Letters*, 467:31-36, 2000.

Neshich et al., "STING Millennium: a web-based suite of programs for comprehensive and simultaneous analysis of protein structure and sequence," *Nucleic Acids Research*, 31:386-392, 2003.

Niemeyer et al., "Self-assembly of DNA-streptavidin naostructures and their use as reagents in immuno-PCR," *Nucleic Acids Research*, 27:4553-4561, 1999.

Pahler et al., "Characterization and crystallization of core streptavidin," *The Journal of Biological Chemistry*, 262:13933-13937, 1987.

Qureshi and Wong, "Design, production and characterization of a monomeric streptavidin and its application for affinity purification of biotinylated proteins," *Protein Expression Purification*, 25:409-415, 2002.

Qureshi et al., "Development and characterization of a series of soluble tetrameric and monomeric streptavidin with differential biotin binding affinities," *The Journal of Biological Chemistry*, 276:46422-46428, 2001.

Sano et al., "Intersubunit contacts made by trypotophan 120 with biotin are essential for both strong biotin binding and biotin-induced tigether subunit association of streptavidin," *Proc. Natl. Acad. Sci. USA*, 92:3180-3184, 1995.

Sano et al., "Recombinant core streptavidins: a minimum-sized core streptavidin has enhanced structural stability and higher accessibility to biotinylated macromolecules," *The Journal of Biological Chemistry*, 270:28204-28209, 1995.

Schechter et al., "Organ selective delivery using a tissue-directed streptavidin-biotin system:targeting 5-fluorouridine via TNP-streptadivin," *Journal of Drug Targeting*, 6:337-348, 1999.

Scholle et al., "In vivo biotinylated proteins as targets for pahge-display selection experiments," *Protein Expression & Purification*, 37:243-252, 2004.

Schwalbe et al., "A refined solution structure of hen lysozyme determined using residual dipolar coupling data," *Protein Science*, 10:667-688, 2001.

Sorensen et al., "A favorable solubility partner for the recombinant expression of treptavindin," *Protein Expression & Purification*, 32:252-259, 2003.

Swint-Kruse et al., "Plasticity of quaternary structure: twenty two ways to form a LacI dimer," *Protein Science*, 10:262-276, 2001.

Szafranski et al., "A new approach for containment of microorganisms: dual control of streptavidin expression by antisense RNA and the T7 transcription system," *Proc. Natl. Acad. Sci. USA*, 94:1059-1063, 1997.

Terpe, "Overview of tag protein fusions: from molecular and biochemical fundamentals to commercial systems," *appl. Microbiol. Biotechnol.*, 60:523-533, 2003.

Vetter et al., "Protein structural plasticity exemplified by insertion and deletion mutants in T4 lysozyme," *Protein Science*, 5:2399-2415, 1996.

Waner et al., "Thermal and sodium dodecylsulfate induced transitions of streptavidin," *Biophysical Journal*, 87:2701-2713, 2004.

Weber et al., "Structural origins of high-affinity biotin binding to streptavidin," *Science*, 243:85-88, 1989.

Wilchek et al., "The avidin-biotin complex in bioanalytical applications," *Analytical Biochemistry*, 171:1-32, 1988.

Wong et al., "Production and purification of antibody using *Bacillus subtilis* as an expression host," *American Chemical Society*, 100-107.

Wu and Wong "Engineering of a *Bacillus subtillis* strain and adjustable levels of intracellular biotein for secretory production of functional streptavidin," *Applied and Environmental Microbiology*, 68:1102-1108, 2002.

Wu et al., "Design, production and characterization of an engineered biotin ligase (BirA) and its application for affinity purification of staphylokinase produced from *Bacillus subtillis* via secretion," *Protein Expression and Purification*, 24:357-365, 2002.

Wu et al., "Engineering soluble monomeric streptavidin with reversible biotin binding capability," *Journal of Biological Chemistry*, 280:23225-23251, 2005.

Wu et al., "Secretory production and purification of functional full-length streptavidin from *Bacillus subtillus*," *Protein Expression and Purification*, 24:348-356, 2002.

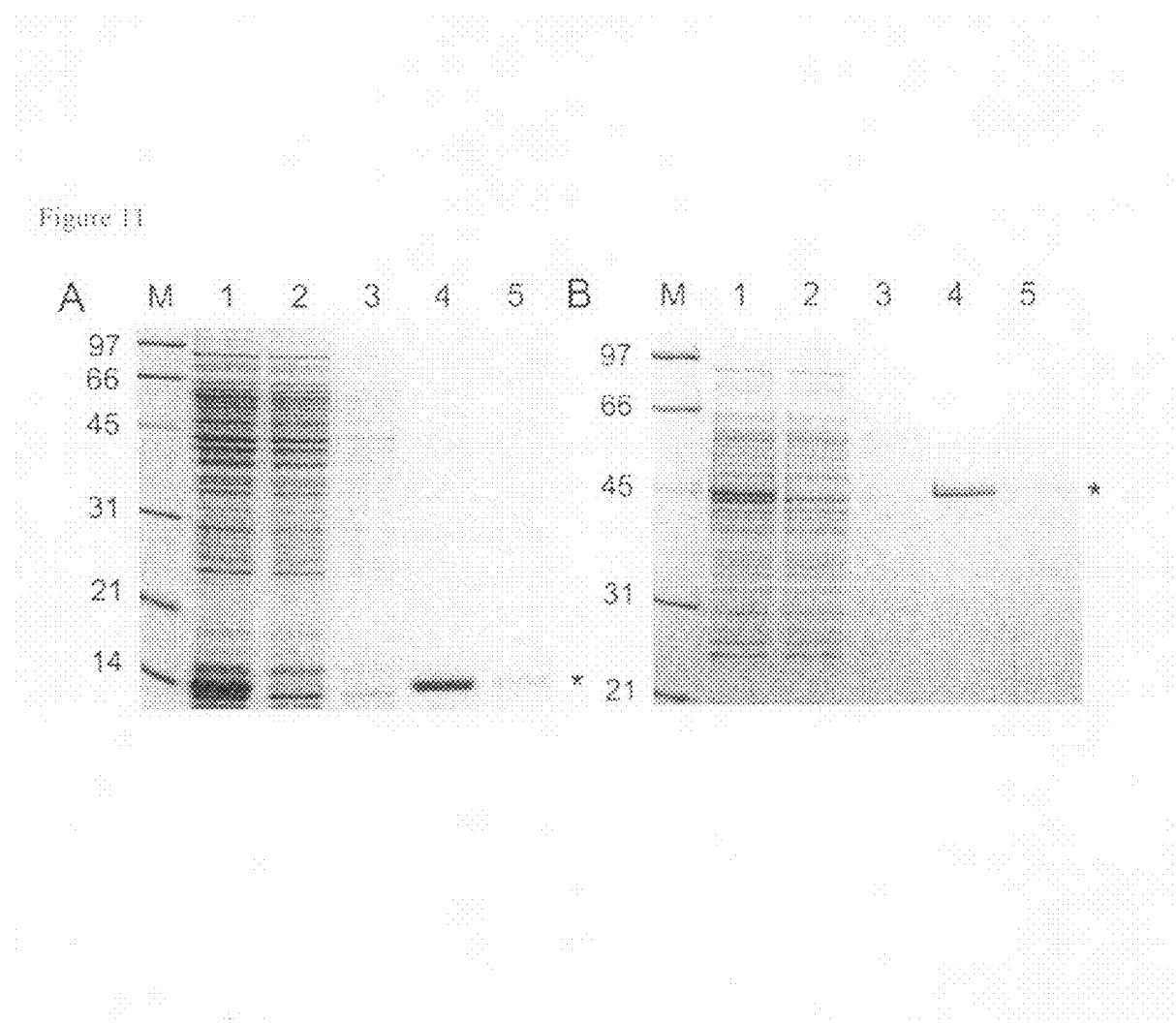

MONOMERIC STREPTAVIDIN MUTEINS

CROSS REFERENCE TO RELATED APPLICATIONS

This application is a division of U.S. patent application Ser. No. 11/307,576 filed on Feb. 13, 2006 entitled "Monomeric Streptavidin Muteins", now U.S. Pat. No. 7,265,205, the contents of which are incorporated herein by reference.

FIELD OF THE INVENTION

The present invention relates to monomeric streptavidin muteins. In particular, the invention relates to production of an engineered monomeric streptavidin for use in the capture and/or purification of biotinylated proteins.

BACKGROUND

High throughput systems have been used to generate affinity tagged recombinant proteins to assist in their immobilization and purification, to study their function and structure. Although a number of tags have been developed, those that can be used efficiently for both purification and immobilization are limited; and biotinylation offers potential for both tasks. The tight binding of biotin to avidin and streptavidin results in capturing of biotinylated biomolecules. The availability of a form of streptavidin in appropriate quantities that binds reversibly, such that it can be used for capture and/or purification of biotinylated proteins in acceptable yield would significantly extend potential applications of biotin-streptavidin technology (Bayer, 1990; Bashir, 2001; Niemeyer, 1999; Schechter, 1999; Casalini, 1997).

Monomeric avidin may be obtained by immobilizing tetrameric avidin molecules on to a matrix followed by denaturation and renaturation (Henrikson, 1979; Kohanski, 1990). The process for denaturation and renaturation is fairly expensive with loss of non-immobilized avidin subunits and the consumption of a large quantity of expensive reagents in the denaturation step. Furthermore, the high stability of avidin and the strong interfacial interactions between avidin subunits make complete denaturation challenging. Any remaining tetrameric avidin molecules in the matrix can lead to reduced recovery of biotinylated molecules during elution (Kohanski, 1990).

Although streptavidin and avidin have similar three-dimensional structures and biotin binding properties, development of monomeric streptavidin is considered more challenging for at least two reasons. First, streptavidin has stronger subunit interfacial interactions than avidin (Bayer, 1996; Waner, 2004). It is more difficult to weaken this strong interface interaction. Second, monomerization of streptavidin may result in the surface exposure of hydrophobic residues, which normally would be buried at the interface in tetrameric streptavidin. This can potentially affect the solubility of the monomeric streptavidin and lead to re-association of the monomers. Solubility is less of an issue for avidin, which is a glycosylated protein with a carbohydrate chain in each of the avidin subunits.

However, engineered versions of monomeric avidin and streptavidin (Qureshi, 2001; Qureshi, 2002) have been developed. These mutations led to weak H-bonding interactions between streptavidin and biotin, and also affected subunit interactions at the interface. However, the low affinity of this mutein towards biotin ($K_d = 1.7 \times 10^{-6}$ M) makes it less than ideal.

Streptavidin is a homo-tetrameric molecule with a biotin binding site in each subunit (Green, 1990). The three dimensional structure of streptavidin (Hendrickson, 1989; Weber, 1989) suggests that a complete biotin binding pocket in each subunit requires the contribution of a tryptophan residue (Trp-120 for streptavidin and Trp-110 for avidin) from an adjacent subunit. Site-directed mutagenesis studies also demonstrate the importance of this residue for tight biotin binding and subunit communications (Freitag, 1998; Sano, 1995; Laitinen, 2001). In the case of avidin, the first generation of engineered monomeric avidin can exist in the monomeric state only in the absence of biotin (Laitinen, 2001). This problem has been solved by the development of a monomeric avidin (Laitinen, 2003), which carries two mutations (N54A, W110K). Structural alignment of avidin and streptavidin indicates that these two residues correspond to D61 and W120 in streptavidin (Livnah, 2003). However, a streptavidin mutein (AK mutein) which carries the corresponding double mutations (D61A, W120K) does not become monomeric (Wu, 2005). Although AK mutein shows reversible biotin binding property and monomeric behavior on the SDS-polyacrylamide gel, it clearly exists in the oligomeric state in solution.

The challenges in producing a monomeric streptavidin mutein, which has useful biotin binding properties, have not yet been completely addressed. There is a need in the art for a streptavidin mutein that may be produced in a soluble and functional form and that reversibly binds to biotinylated biomolecules, which can then be used for capture and/or purification of biotinylated biomolecules.

SUMMARY OF THE INVENTION

The present invention relates to the engineering and production of a monomeric streptavidin, referred to herein as a mutein. In a preferred embodiment, the invention relates to the engineering and production of monomeric streptavidin mutein using a suitable expression system and host cell such as *B. subtilis* or *E. coli*. In one embodiment, the monomeric streptavidin mutein includes site-specific mutation or mutations that allow for formation of the monomer and reversibly bind to biotin.

The mutein may be used for the capture and purification of biomolecules. In a preferred embodiment, the engineered monomeric streptavidin reversibly interacts with biotinylated biomolecules and assist with their capture and purification.

The inventors have determined that a mutation of a residue located on a rigid surface, to introduce either charge repulsion and steric hindrance, or both, at the interface, can be effective in developing monomeric streptavidin. The efficiency of streptavidin monomerization may be further enhanced by introducing a second mutation (M2). In a preferred embodiment, further mutations may be introduced to ensure that the streptavidin mutein will stably remain in the monomeric state and in solution.

Therefore, in one aspect, the invention may comprise a streptavidin mutein comprising at least one mutation chosen to cause one or more of steric hindrance, charge repulsion, or improvement of solubility by changing interfacial hydrophobic residues to less hydrophobic or hydrophilic residues. In one embodiment, the mutein comprises an amino acid sequence comprising a mutation wherein Thr76 is substituted with a charged amino acid. The mutein may further comprise at least one mutation of a hydrophobic interfacial amino acid residue to a less hydrophobic, charged or hydrophilic residue. In one embodiment, at least one mutation is selected from the group consisting of:

(a) Val125 substituted with a charged or hydrophilic amino acid;

(b) Val55 substituted with a charged or hydrophilic amino acid; and (c) Leu109 substituted with a charged or hydrophilic amino acid.

In a preferred embodiment, the mutein comprises at least four mutations where Thr76 is substituted with Arg, Val125 is substituted with Arg, Val55 is substituted with Thr; and Leu109 is substituted with Thr. In another aspect, the invention may comprise a polynucleotide which encodes for a streptavidin mutein as described herein, an expression vector comprising such polynucleotides, or a host cell comprising such an expression vector. The host cell may comprise *B. subtilis* or *E. coli*.

In another aspect, the invention may comprise a method of isolating a biotinylated molecule from a sample, comprising the steps of binding a streptavidin mutein as described herein to a solid support to form a matrix, passing the sample over the support, and eluting the biotinylated molecule. The solid support matrix may then be regenerated for reuse.

BRIEF DESCRIPTION OF THE DRAWINGS

Exemplary embodiments of the invention may be described with reference to the following figures.

FIG. 2A. Interfaces of tetrameric streptavidin. Subunit A forms three subunit contact interfaces with other subunits. These interfaces include A/B, A/C and A/D. Subunits A, B, C and D are highlighted in red, orange, yellow and green, respectively. FIG. 2B. Local environment of Thr-76 in subunit A. This shows the interfacial interaction between subunits A and B. Thr-76 in subunit A is close to both Thr-76 and Arg-59 in subunit B. Thr-75 and Arg-59 in subunit A are highlighted in red and pink, respectively. Thr-76 and Arg-59 in subunit B are in dark and bright yellow, respectively. FIG. 2C. Local environment of Val-125 in subunit A. This shows the interfacial interaction between subunit A and D. Val-125 highlighted in red fits into a pocket formed by Val-125 (green) and Thr-123 (green) from subunit D. FIG. 2D. Local environment of Val-125 in subunit A. Val-55 (red) in subunit A is close to Arg-59 (yellow) in subunit B.

FIG. 4A. Coomassie blue stained SDS-polyacrylamide gel. Bands corresponding to tetrameric and monomeric streptavidin are marked by an asterisk and an arrowhead, respectively. FIG. 4B. Western blot probed with polyclonal antibodies against streptavidin. M, molecular weight markers; wt, wild type streptavidin; AK, mutein (D61A, W120K); M1, mutein (T76R); M2, mutein (T76R, V125R); M4, mutein (T76R, V125R, V55T, L109T); C, negative control.

FIG. 6A. Determination of apparent molecular mass of streptavidin muteins in the absence of biotin using Bio-Prep SE 100/17 gel filtration column. Bovine gamma-globulin (158 kDa), bovine serum albumin (66 kDa), ovalbumin (44 kDa), myoglobin (17 kDa) and vitamin B-12 (1.35 kDa) were used as molecular mass markers (closed circles) to calibrate the column. The logarithm of molecular mass was plotted versus $K_{av}$ ($K_{av}=(V_e-V_o)/(V_t-V_o)$; $V_e$, elution volume; $V_o$, void volume; $V_t$, bed volume). Positions of wild-type streptavidin (wt) and streptavidin muteins are represented by solid squares. FIG. 6B. Elution profile of M4 mutein (loaded at 2 mg/ml) on the gel filtration column.

FIG. 7A. Proteinase K digestion. FIG. 7B. Cross-linking study using sulfo-EGS as the cross-linker. All samples were boiled prior to loading. M, molecular weight markers; wt, wild type streptavidin; L, lysozyme. Numbering represents streptavidin molecules in monomeric (1), dimeric (2) and oligomeric (3-5) states, respectively.

FIG. 11: Coomassie blue-stained SDS-polyacrylamide gel showing purification of biotinylated proteins using M4 affinity column. FIG. 11A Purification of biotinylated cytochrome c. Asterisk marks the position of the cytochrome c. FIG. 11B Purification of biotinylated MBP-AviTag. Asterisk marks the position of the MBP-aviTag. Lane M, molecular weight markers. Lane 1, crude sample containing *B. subtilis* cell lysate and biotinylated protein. Lane 2, column flow-through. Lane 3, one-column wash. Lanes 4 and 5, eluted fractions.

DETAILED DESCRIPTION OF PREFERRED EMBODIMENTS

Figure 1:
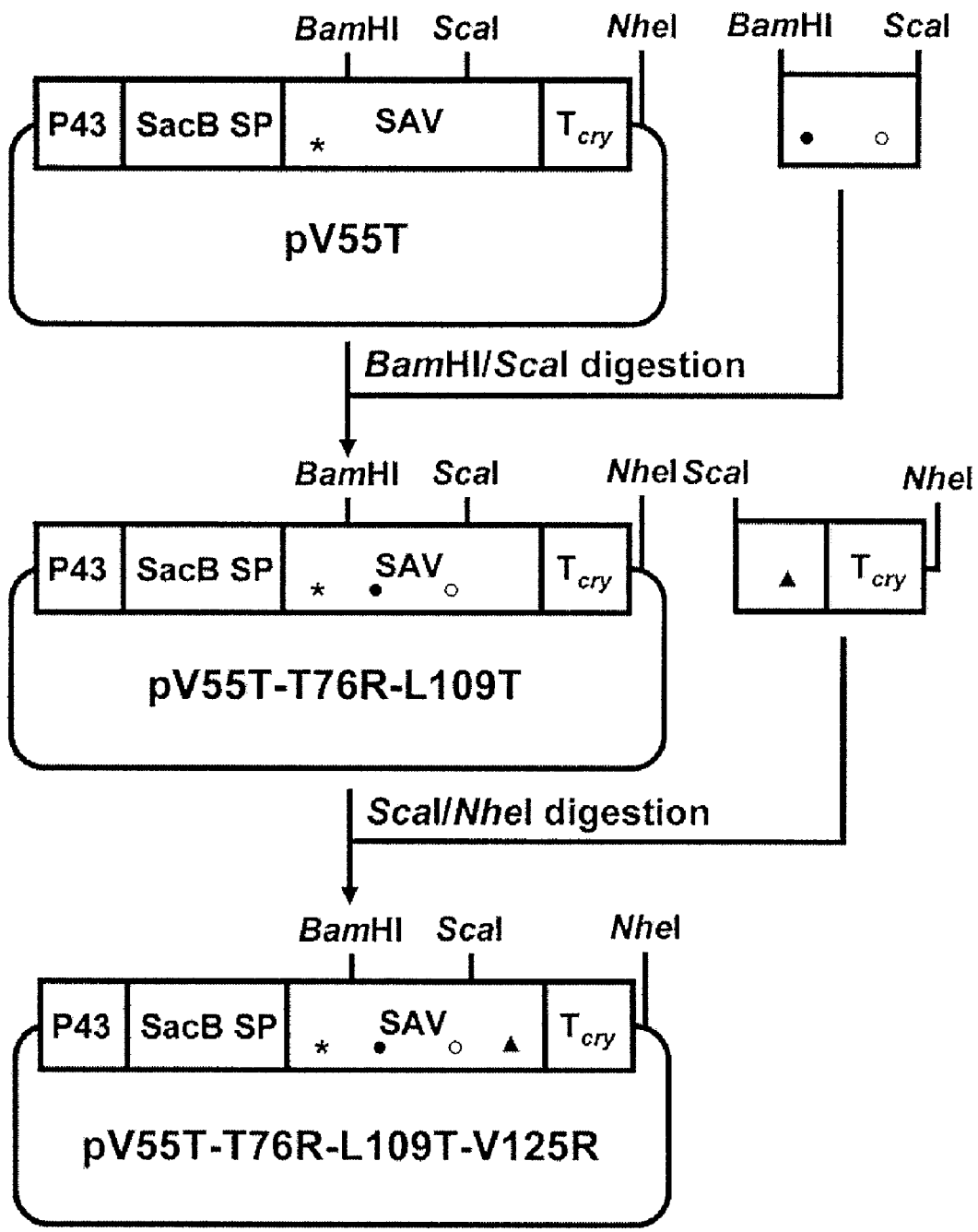
FIG. 1: Construction of the pV55T-T76R-L109T-V125R expression vector for the production of a streptavidin mutein M4. The restriction sites used in construction are indicated. The 164-bp BamHI/ScaI fragment bearing T76R and L109T mutations was generated through PCR. The ScaI/NheI fragment carrying the V125R mutation was from pV125R. P43, P43 promoter; SacB SP, *B. subtilis* levansucrase signal peptide; Tcry, the transcription terminator from the *Bacillus thuringiensis* crystal toxin gene; SAV, synthetic streptavidin gene. Asterisk, closed circle, open circle and closed triangle represent V55T, T76R, L109T and V125R mutations, respectively.

The present invention provides for a streptavidin mutein having useful properties. As used herein, a "mutein" means a genetically engineered protein arising as a result of a laboratory-induced mutation. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

As used herein, "streptavidin" refers to wild-type protein, and includes naturally occurring variants thereof. The reference to amino acid positions herein refers to the amino acids in the mature streptavidin protein, from which the signal sequence has been removed, the sequence of which is reproduced below, and obtained from GenBank (National Center for Biotechnology Information, USA), for example as Accession #X03591 or #AF283893.

skilled in the art, an example of which is disclosed in the Examples herein. As is known in the art, $K_d$ is related to the association constant $K_a$, being the inverse thereof.

As used herein, "lower binding affinity" means a decrease in the binding affinity relative to streptavidin, which can be measured as an increase in $K_d$ or, alternatively, a decrease in $K_a$. The lower binding affinity can result from a change in one or both of $k_{on}$ (the "on rate", or "association rate constant", or $k_a$) and $k_{off}$ (the "off rate", or "dissociation rate constant", or $k_d$).

As used herein, "monomeric form" or "monomer" means a streptavidin or mutein subunit that is not in the form of a complex with another streptavidin or mutein subunit, or that does not form a complex with another streptavidin or mutein subunit.

TABLE 1

```
SEQ ID. NO: 1 (mature monomeric streptavidin subunit protein sequence)
            10         20         30         40         50         60
             |          |          |          |          |          |
  1 DPSKDSKAQV SAAEAGITGT WYNQLGSTFI VTAGADGALT GTYESAVGNA ESRYVLTGRY

61 DSAPATDGSG TALGWTVAWK NNYRNAHSAT TWSGQYVGGA EARINTQWLL TSGTTEANAW

121 KSTLVGHDTF TKVKPSAASI DAAKKAGVNN GNPLDAVQQ
```

Reference herein to the streptavidin nucleic acid or polynucleotide, and nucleotide positions therein, is a reference to any nucleic acid encoding streptavidin, and includes, for example the wild-type nucleic acid (SEQ ID NO: 2) or a synthetic nucleic acid (SEQ ID NO:3)

As used herein, "tetrameric form" or "tetramer" means a protein complex that is comprised of four streptavidin and/or mutein subunits, and includes complexes in which one or more of the four subunits are different from one another.

TABLE 2

```
SEQ ID. NO: 2
            10         20         30         40         50         60
             |          |          |          |          |          |
  1 CCCTCCGTCC CCGCCGGGCA ACAACTAGGG AGTATTTTTC GTGTCTCACA TGCGCAAGAT

61 CGTCGTTGCA GCCATCGCCG TTTCCCTCAC CACGGTCTCG ATTACGGCCA GCGCTTCGGC

121 AGACCCCTCC AAGGACTCGA AGGCCCAGGT CTCGGCCGCC GAGGCCGGCA TCACCGGCAC

181 CTGGTACAAC CAGCTCGGCT CGACCTTCAT CGTGACCGCG GGCGCCGACG GCGCCCTGAC

241 CGGAACCTAC GAGTCGGCCG TCGGCAACGC CGAGAGCCGC TACGTCCTGA CCGGTCGTTA

301 CGACAGCGCC CCGGCCACCG ACGGCAGCGG CACCGCCCTC GGTTGGACGG TGGCCTGGAA

361 GAATAACTAC CGCAACGCCC ACTCCGCGAC CACGTGGAGC GGCCAGTACG TCGGCGGCGC

421 CGAGGCGAGG ATCAACACCC AGTGGCTGCT GACCTCCGGC ACCACCGAGG CCAACGCCTG

481 GAAGTCCACG CTGGTCGGCC ACGACACCTT CACCAAGGTG AAGCCGTCCG CCGCCTCCAT

541 CGACGCGGCG AAGAAGGCCG GCGTCAACAA CGGCAACCCG CTCGACGCCG TTCAGCAGTA

601 GTCGCGTCCC GGCACCGGCG GGTGCCGGGA CCTCGGCC
```

In the nucleotide sequence for the wild type streptavidin subunit, the precursor sequence is between nucleotides 50-598. The coding sequence for the mature wild type streptavidin subunit is between nucleotides 122-598. The translation stop codon is located between nucleotides 599-601.)

As used herein, "affinity" refers to the dissociation constant ($K_d$) of a complex between a mutein or streptavidin, and biotin, as determined by standard methods known to those As used herein, "subunit" means the protein that is generated from a streptavidin or mutein gene. "Subunit" is used interchangeably with "monomer".

As used herein, "biotin" means biotin in its free form as well as in the form of biotinylated substances such as biotinylated nucleic acids, carbohydrates, lipids, peptides or polypeptides, biotin analogues and biotin derivatives such as iminobiotin, desthiobiotin and streptavidin affinity peptides.

As used herein, amino acids shall be referred to their commonly accepted abbreviations as well as their numerical position as indicated by SEQ ID NO: 1. As may be appreciated, if amino acid substitutions or deletions are made in mutein of this invention, the numerical position of a particular amino acid in the mutein may be altered.

Figure 2:
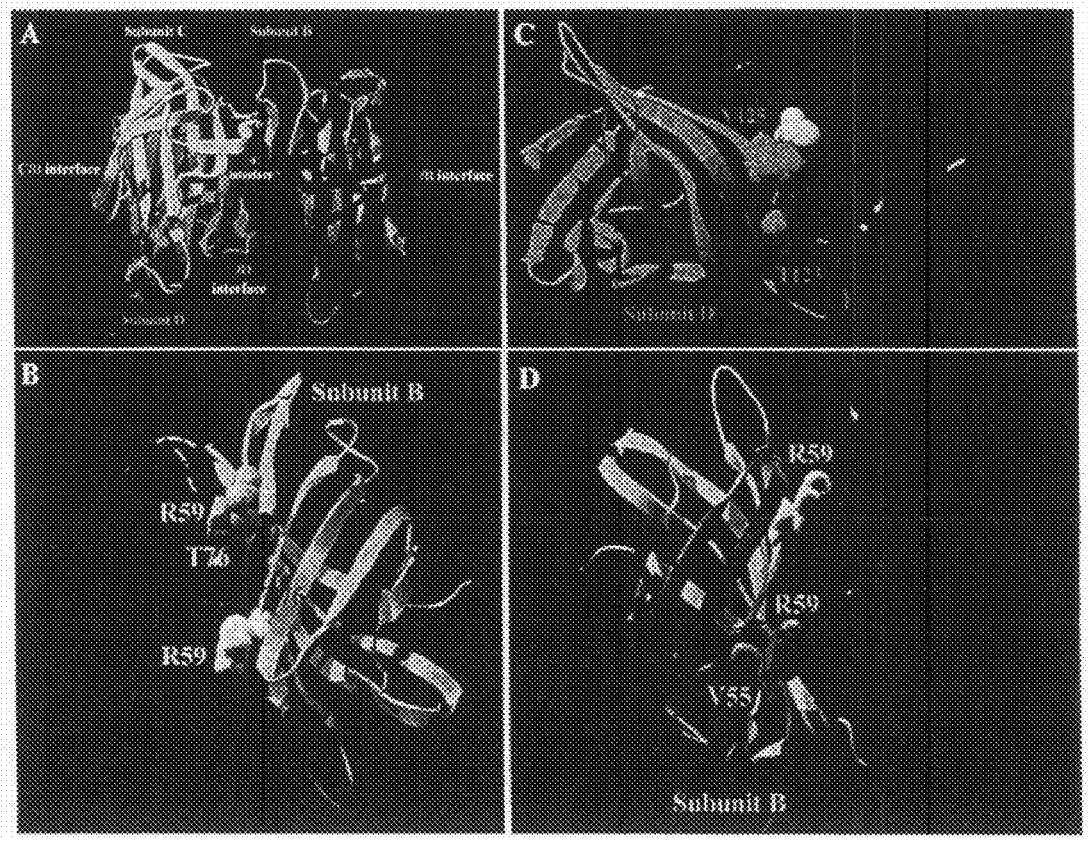
FIG. 2: Structure of tetrameric streptavidin and critical interface residues selected for mutagenesis.

As shown in the FIG. 2, the interface between subunits A and B (and between C and D) has the most extensive subunit interactions. The interfacial contact area between A and B is ~1,557 Å$^2$ with 17H-bonding interactions, two salt bridges and numerous van der Waal interactions. The interface contact between A and D is also extensive with a contact area of 525 Å$^2$ and two interfacial H-bonding interactions. The weakest interface interaction is between subunits A and C with an interfacial contact area of 171 Å$^2$.

The present invention incorporates mutations designed to introduce charge repulsion, steric hindrance, or hydrophilicity, or combinations thereof, in order to achieve useful properties. As proteins are known to have structural plasticity, it is preferred to select interfacial residues located on a rigid surface to maximize the effects of charge repulsion and steric hindrance. Since streptavidin subunit forms an eight-antiparallel stranded β-barrel structure (Weber, 1989; Hendrickson, 1989), the selected residues are preferably located on the β-strands rather than in the loop regions. Furthermore, in preferred embodiments, the selected residue in one subunit should be located very close to the equivalent residue or a charged residue in another subunit at the interface. The exposure of the AB (or CD) interface will expose hydrophobic residues. Based on the above criteria and upon examination of interfacial residues (FIGS. 2B-D), four amino acids in particular, Thr-76, Val-125, Val-55, and Leu-109 meet at least one criterion. Hence, in a preferred embodiment, these four are preferred candidates for mutagenesis.

The monomeric muteins of streptavidin may be made using methods known to those skilled in the art, for example by cassette mutagenesis of streptavidin and expression of the mutated streptavidin gene in an appropriate host, an example of which is included in the Examples herein. As is apparent, different PCR primers than those used in the Examples herein may be used, and will likely be needed, if one is using as a PCR template a nucleic acid for streptavidin that is different than the synthetic ssav gene, for example the wild-type gene for streptavidin, or another gene that codes for streptavidin. Those skilled in the art know how to design alternative primers for use in making the mutein herein. The affinity of the monomeric mutein of streptavidin for biotin can be measured using techniques known to those skilled in the art, for example by using a surface plasmon resonance (SPR) based BIAcoreX™ biosensor, as disclosed in the Examples herein.

Streptavidin muteins carrying a single amino-acid change at the selected site may be produced in their soluble form by *B. subtilis* via secretion. Analysis of non-boiled culture supernatants by SDS-PAGE offers a quick screen for the mutation effect (Qureshi, 2001). Weaker subunit interaction would result in a higher percentage of the sample in the monomeric state on the SDS-polyacrylamide gel. Since biotin can strengthen subunit interaction, samples were analyzed in the presence or absence of biotin (Laitinen, 2001; Gonzalez, 1999).

As demonstrated in the Examples, a single mutation is sufficient to cause a mutein to exist as a monomer, even in the presence of biotin. In one embodiment, the mutation is a substitution of Thr76 (T76). Without being bound to a theory, it is believed that because this residue has a solvent accessible area of zero, exists close to both T76 and Arg-59 in subunit B and is located on a rigid surface of a β-barrel structure, it is an ideal residue to be changed in the present invention. In a preferred embodiment, it is changed to an amino acid with a relatively bulky and charged side chain, such as arginine, lysine or histidine, to achieve the maximal electrostatic repulsion and steric hindrance effects at the subunit interface. In another embodiment, the mutation is a substitution of Val-125, which has a solvent accessible area in subunit A of 1.78%. It has extensive interactions with Leu-109, Trp-120, Thr-123 and Val-125 in subunit D (FIG. 2C), Leu-109 in subunit B and Gln-107 in subunit C. Its conversion to an amino acid with a relatively bulky and charged side chain, such as arginine, lysine or histidine, results in charge repulsion in subunit D and potential steric hindrance for subunits B, C, and D.

When choosing substitutes for muteins of the present invention, charged amino acids may be either positively or negatively charged amino acid residues. Positively charged amino acids may be preferred. In addition to the potential charge repulsion effect, charged amino acids are hydrophilic, which may aid in the solubility of the resulting mutein.

In a preferred embodiment, a second mutation may be added to develop monomeric streptavidin muteins that are more likely to remain in the monomeric state at high streptavidin concentrations, in the presence of biotin, and have excellent reversible biotin binding capability. A double mutant carrying both T76 and V125 mutations is referred to herein as M2. In one example, M2 carries T76R and V125R mutations.

In another preferred embodiment, additional mutations are possible. Preferably, one or more additional interfacial amino acids are changed. A quadruple mutant carrying T76, V125, V55 and L109 mutations is referred to herein as M4. In one example of M4, in addition to the two mutations of M2, two additional interfacial hydrophobic residues Val-55 and Leu-109 are changed to hydrophilic amino acids. Therefore, in one example, M4 carries T76R, V125R, V55T and L109T mutations. Other mutations of interfacial hydrophobic residues to less hydrophobic, or hydrophilic residues are within the scope of the present invention.

Figure 4:
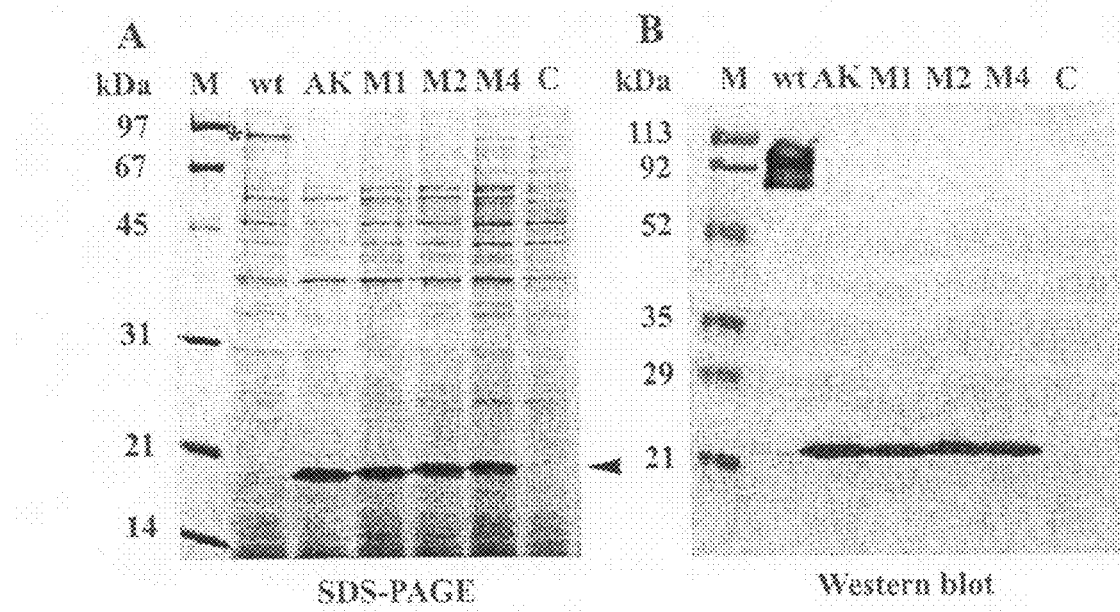
FIG. 4: Analysis of culture supernatants from *B. subtilis* strains producing streptavidin muteins carrying different combinations of mutations. All these strains were cultivated in super-rich medium supplemented with biotin (20 μM). The 15 μl of non-boiled samples of culture supernatants were loaded.
Figure 5:
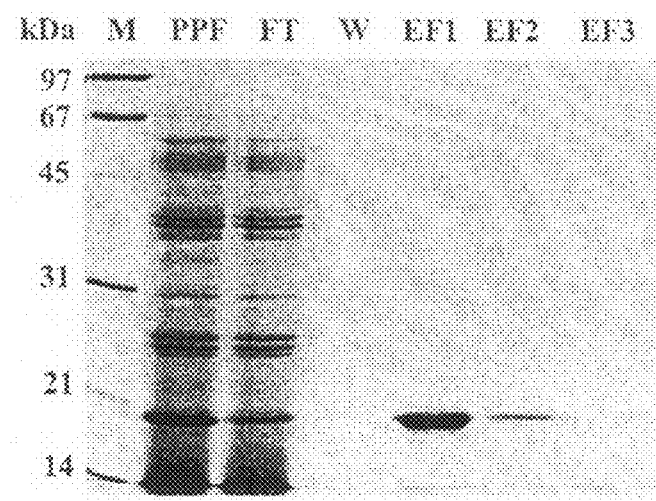
FIG. 5: Purification of the M4 streptavidin mutein using biotin-agarose. M4 mutein partially purified by Macro S column chromatography (PPF) was loaded on a biotin-agarose column. M, molecular weight markers; FT, column flowthrough; W, pooled washing fractions; EF1-EF3, eluted fractions.

As shown in FIG. 4 and Table 4, examples of M2 and M4 exist in monomeric state on the SDS-polyacrylamide gel even in the presence of biotin.

In one example of a M2 mutein, Val-125 has been changed to arginine. Val-55 and Leu-109 may be changed to a more hydrophilic residue, such as threonine, as in a M4 mutein embodiment. Conversion to threonine instead of arginine is preferred because proteins with high pI are known to have non-specific interactions via electrostatic interactions (Marttila, 1998; Marttila, 2000). The calculated pI of M2 (V55T, L109T) is 8.1. If both Val-55 and Leu-109 are converted to arginine, the resulting mutein will have a pI of 9.2. This may increase the chance of charge-related non-specific interactions. The conversion of these residues to negatively charged residues is possible, but not preferred because both Val-55 and Leu-109 are located on the β-strands and negatively charged residues are relatively poor β-strand formers.

M4 mutein, like M2 mutein, exists in the monomeric state at a reasonably high protein concentration (2 mg/ml or more as used in dynamic light scattering study). Both have excellent reversible biotin binding capability as reflected by their on-rate and off-rate for biotin interaction. Both have a moderate pI value of 8.1 so that charge-related non-specific interactions will be minimal. M4 is a preferred embodiment as it displays additional two features. Molecules of M4 mutein are less likely to aggregate in solution. M2 is preferably filtered through a 0.02 μm filter in order to obtain a good signal of the mutein for dynamic light scattering studies because of poor signal detection caused by the presence of small amounts of large aggregates in an unfiltered sample. Good results may be obtained with M4 with an unfiltered sample of similarly prepared M4. Thus, conversion of the two hydrophobic residues (Val-55, Leu-109) to the more hydrophilic threonine residue does assist in minimizing aggregation of the mutein. Also, M4 has a sharp elution profile with its purification using biotin-agarose. Over 95% of the mutein could be readily eluted off from the column using just two column volumes of the eluant, leading to a high rate of protein recovery.

Muteins of the present invention may include additional amino or carboxyl-terminal amino acids, or amino acids interior to the mutein (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed from the engineered protein by cellular enzymes.

Muteins of the present invention may also include insubstantial variants such as those carrying silent substitutions, additions and deletions that do not significantly alter the properties and activities of the mutein.

In another aspect of the invention, the invention comprises polynucleotides that encode the streptavidin muteins described herein. Such polynucleotides may encode the amino acid sequence set out in Table 1 [SEQ ID NO: 1] with one or more of the selected mutations. The polynucleotides of the present invention may include, for example, unprocessed RNAs, ribozyme RNAs, mRNAs, cDNAs, genomic DNAs, B- and Z-DNAs.

A preferred polynucleotide comprises the nucleotide sequence shown in Table 2 [SEQ ID NO: 2] with mutations which encodes the muteins described herein. Other polynucleotides included in the present invention may encode biologically active variants of the muteins.

Using the information provided herein, such as a polynucleotide sequence set out in Table 2 [SEQ ID NO: 2], the portion of the polynucleotide of the invention encoding streptavidin may be obtained using standard screening and cloning methods. For example, to obtain a polynucleotide fragment comprising some of all of the streptavidin sequence, a *Streptomyces* species chromosomal DNA library is probed by hybridization with a synthetic radiolabeled oligonucleotide, preferably a 17-mer or longer, that is homologous to the streptavidin sequence. Clones carrying DNA highly homologous to the probe are identified by using stringent hybridization conditions. By sequencing the individual clones identified by hybridization with sequencing primers designed from the sequences in the plasmid or phage DNA from which the library was constructed, it is possible to identify the streptavidin clones. The DNA inserts from several clones can be ligated together to obtain a full-length polynucleotide, if necessary. Suitable techniques for manipulating DNA are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70).

The invention may provide a coding sequence for a mature protein or a portion thereof, by itself, as well as a coding sequence for a mature protein or a portion thereof in frame with another coding sequence, such as a sequence encoding a leader or secretory sequence, a pre-, or pro- or prepro-protein sequence. The polynucleotides of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids.

The term "polynucleotide encoding a polypeptide" as used herein encompasses polynucleotides that include a sequence encoding a mutein of the present invention. The term also encompasses polynucleotides that include a single continuous region or discontinuous regions encoding the engineered protein (for example, polynucleotides interrupted by integrated phage, an integrated insertion sequence, an integrated vector sequence, an integrated transposon sequence, or due to RNA editing or genomic DNA reorganization) together with additional regions that also may contain coding and/or non-coding sequences.

Preferred embodiments include polynucleotides encoding proteins that retain substantially the same biological function or activity as a M1, M2 or M4 mutein described herein. Further particularly preferred embodiments are polynucleotides encoding variants of M1, M2 or M4 muteins, in which several, a few, 5 to 10, 1 to 5, 1 to 3, 2, 1 or no amino acid residues are substituted, modified, deleted and/or added, in any combination. Especially preferred among these are silent substitutions, additions and deletions that do not alter the properties and activities of the mutein.

Other preferred embodiments of this invention may include polynucleotides that hybridize, particularly under stringent conditions, to polynucleotides described herein including polynucleotide sequences encoding the engineered protein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The invention also provides polynucleotides that encode a polypeptide that is the mutein plus additional amino or carboxyl-terminal amino acids, or amino acids interior to the mutein (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed from the engineered protein by cellular enzymes.

For each and every polynucleotide of the invention there is provided a polynucleotide complementary to it. It is preferred that these complementary polynucleotides are fully complementary to each polynucleotide with which they are complementary.

In addition to the standard A, G, C, T/U representations for nucleotides, the letter "N" may also be used in describing a nucleotide. "N" means that any of the four DNA or RNA nucleotides may appear at such a designated position in the DNA or RNA sequence, except it is preferred that N is not a nucleic acid that, when taken in combination with adjacent nucleotide positions, when read in the correct reading frame, would have the effect of generating a premature termination codon in such reading frame.

In sum, a polynucleotide of the invention may encode the muteins described herein, the muteins plus a leader sequence (which may be referred to as a preprotein), or a precursor of the mutein, having one or more prosequences that are not the leader sequences of a preprotein, or a preproprotein, which is a precursor to a proprotein, having a leader sequence and one or more prosequences, which generally are removed during processing steps that produce active and mature forms of the mutein polypeptide, and insubstantial variants of these polypeptides.

The streptavidin muteins of the present invention may be produced at a reasonable level (50-60 mg/liter) in a prokaryotic expression system, such as *B. subtilis* via secretion (Wu, 2005). In a preferred embodiment, in order to affinity purify the protein using biotin-agarose, the culture supernatant containing the secreted streptavidin mutein is reduced to a manageable volume and freed of biotin contaminants, by dialysis or other means.

Figure 9:
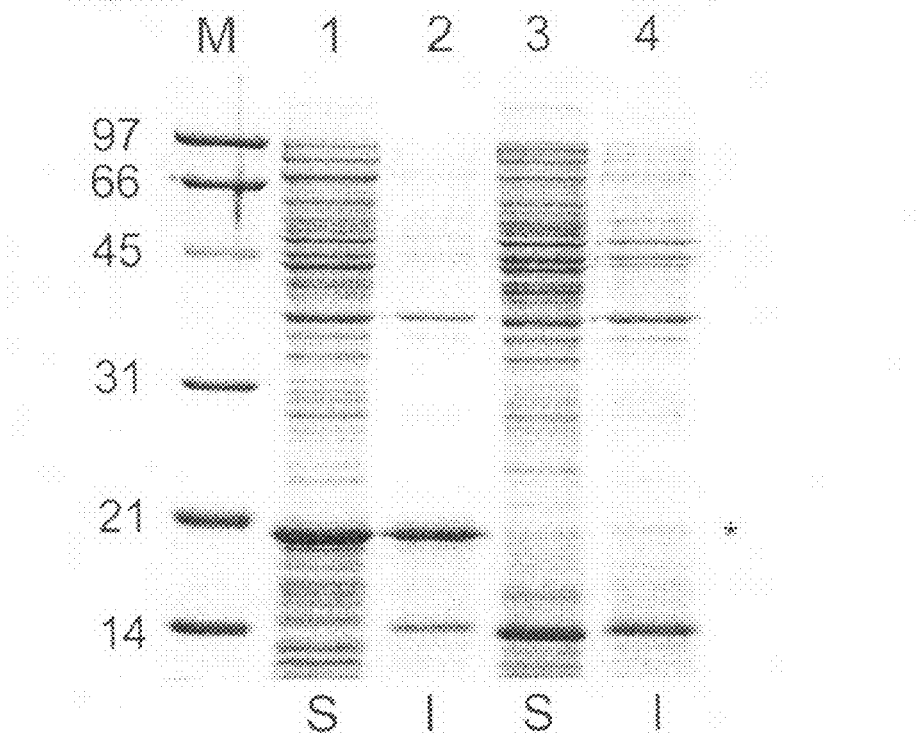
FIG. 9: Coomassie blue-stained SDS-polyacrylamide gel showing intracellular production of monomeric streptavidin in *E. coli*. Samples loaded were not boiled. Lane M, molecular weight markers. Lane 1 and 2, *E. coli* BL21[pET-SAVM4]. Lanes 3 and 4, negative control, *E. coli* BL21 [pET29b]. S, soluble fraction; I, insoluble fraction. Asterisk marks the position of the M4 mutein.

In one embodiment, intracellular production in *E. coli* offers an alternative approach. Toxicity arising from depletion of intracellular biotin by soluble streptavidin (Szafranski, 1997) is not a significant concern since the streptavidin muteins of the present invention have much lower affinity towards biotin. Despite loss of mutein in the insoluble fraction (40-50%), the soluble portion represents a relatively high production yield (around 70 mg/liter) of mutein (FIG. 9). Thus, in one embodiment, with approximately 70% recovery of purified M4 using biotin-agarose chromatography (FIG. 10), 40-50 mg of purified M4 could be obtained from one liter of cell culture.

In order to produce streptavidin mutein intracellularly in *E. coli* in the soluble form, it is preferred to use the mutein gene encoding the full-length version of streptavidin. Streptavidin and its muteins are traditionally produced intracellularly in *E. coli* in a truncated form known as core streptavidin (Pahler, 1987; Sano, 1995; Hyre, 2000; Freitag, 1998; Sano, 1995). This is because the core version represents the form of streptavidin that can be crystallized well for X-ray crystallographic studies. It is also one of the shortest versions of streptavidin that retains full biotin binding capability. However, these core streptavidin molecules predominantly form inclusion bodies. The full-length version (159 amino acids—SEQ ID NO: 1) has a 13 amino-acid extension at the N-terminus and a 20 amino-acid extension at the C-terminus (Pahler, 1987; Sano, 1995; Bayer, 1990). The amino acids in these terminal peptides are mainly charged and polar. Although these sequences are not required for biotin binding, their presence clearly helps minimize the formation of inclusion bodies. This is particularly true when streptavidin is overproduced intracellularly. In one embodiment, various solubility partners such as translation initiation factor IF2, maltose binding protein, NusA, and T7 tag may be fused to streptavidin and can improve the intracellular production of streptavidin in its soluble form (Sorensen, 2003; Gallizia, 1998). In many cases, removal of the fusion partner is required to bring streptavidin back to its original size. Therefore, the use of the natural N- and C-terminal segments from streptavidin is preferred to address the solubility problem associated with streptavidin production. The change of three interfacial hydrophobic residues in M4 changed to either charged or hydrophilic residues, results in excellent solubility even at a concentration of 2 mg/ml (Wu, 2005).

Figure 10:
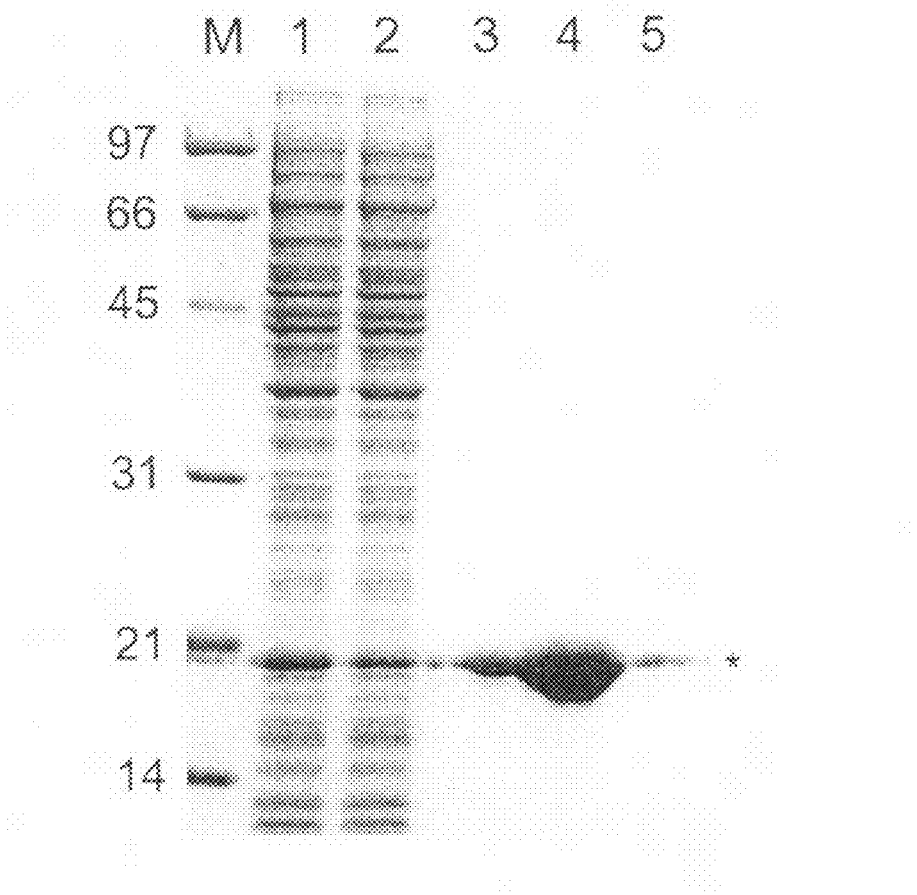
FIG. 10: Purification of M4 mutein using biotin-agarose column. Lane M, molecular weight markers. Lane 1, soluble fraction of crude lysate. Lane 2, column flow-through. Lanes 3-5, eluted fractions. Asterisk marks the position of the M4 mutein.

In one embodiment, *E. coli* cells expressing streptavidin muteins may be harvested and disrupted with a French press in a known manner. The crude cell lysate may be separated into soluble and insoluble fractions by centrifugation. The soluble fraction is dialysed to remove any biotin contaminants and monomeric streptavidin in the dialysate may be purified using known techniques, such as on a biotin-agarose column (FIG. 10).

Muteins of the present invention may be purified by techniques well known to those skilled in the art. In one embodiment, the muteins may e partially purified by ion exchange chromatography, and then further purified on a biotin-agarose column, for example. Muteins may be eluted off from such a column using biotin containing buffer as the eluant. Pure streptavidin mutein obtained by this simple procedure, after removal of biotin by dialysis, may then be used for biochemical characterizations.

Pure monomeric streptavidin muteins may be used to prepare affinity matrices for the purification of biotinylated proteins. A mutein of this invention can be coupled to a solid support using any one of a number of methods known to those skilled in the art, an example of which is disclosed in the Examples herein. "Solid support" as used herein includes any support that immobilizes the mutein of the invention, and includes specifically matrices or polymers such as agarose, polyacrylamide, cellulose, hydroxyapatite or dextran, surfaces of glass, plastic, silicone, ceramics or metals. The solid support may directly form a covalent bond with the mutein or it may be derivatized with a moiety that can form a covalent chemical bond with the mutein. An example of this type of covalent bond is the crosslinking via a carboxyl group, using crosslinking agents such as cyanogen bromide, glutaraldehyde, or hydroxysuccinimide. Alternatively, the solid support may be derivatized with a moiety that can form a near covalent bond with the mutein, for example an antibody to streptavidin.

Once immobilized to the solid support, the mutein will selectively bind biotin, for example in a mixture of biomolecules, and will release the bound biotin under relatively mild conditions, which do not destroy the biological activity of the biotin. In a preferred embodiment, the bound biotin is released by competition with another biotin moiety, however, other gentle methods including elution with salts, or by adjustment of pH, are intended to be included herein, and are known by those skilled in the art.

Biotinylated proteins may be purified by M4-agarose to high purity with a 75-80% recovery (FIG. 11). The operation is simpler than using monomeric avidin-agarose, which requires biotin pretreatment to saturate the non-exchangeable biotin binding sites in the matrix (Kohanski, 1990). Furthermore, recovery of some biotinylated proteins from the monomeric avidin-agarose is better achieved by elution with a solution of low pH. As well, regeneration of the matrix is usually achieved by washing at low pH. This exposure to extreme pH limits the potential application and durability of the monomeric avidin-agarose. The mild conditions in elution and regeneration with M4-agarose of the present invention are more likely to preserve biological activities of both the biotinylated proteins and the monomeric streptavidin in the matrix. One consequence of the mild conditions is that the M4-agarose matrix may be reused without any detectable loss in binding capacity.

EXAMPLES

The examples below are carried out using standard techniques, which are well known and routine to those skilled in the art. These examples are intended to be illustrative, but not limiting, of the invention.

Example 1

Construction of Streptavidin Mutants

Different point mutations were introduced to the coding sequence of a synthetic streptavidin gene (ssav) (SEQ ID NO:3) in the *B. subtilis* expression vector pSSAV-Tcry (Wu, 2002) by PCR-based oligonucleotide-directed mutagenesis. Five mutants (V125R, V125T, V55R, V55T and T76R), each bearing a single mutation which results in the change of an amino acid residue as the name suggests, were constructed using pSSAV-Tcry as the template and the primers listed in Table 3. The amplified products were digested with the pair of enzymes listed in Table 3 and cloned into pSSAV-Tcry. Five plasmids (pV125R, pV125T, pV55R, pV55T and pT76R) resulted.

Two double mutants (M2 and prior art AK) were also constructed. For M2 (T76R, V125R), a ScaI/NheI digested fragment of pV125R was used to replace the corresponding fragment in pT76R. For AK (D61A, W120K), the fragment bearing the two mutations was amplified by PCR using the primers SAVD61AF and SAVW120KB (Table 3) and the template pSSAV-Tcry. The amplified fragment was digested by XbaI/ScaI and used to replace the corresponding fragment in pSSAV-Tcry.

The construction of M4 (T76R, V125R, V55T, L109T) involved two steps (FIG. 1). First, a 164-bp fragment bearing two mutations (T76R, L109T) was amplified using SAVT76RF and SAVL109TB (Table 3) as primers and pSSAV-Tcry as template. The amplified product was digested by BamHI/ScaI and used to replace the corresponding fragment in pV55T to generate pV55T-T76R-L109T. In the second step, a ScaI/NheI digested fragment of pV125R was used to replace the corresponding fragment in pV55T-T76R-L109T to generate pV55T-T76R-L109T-V125R.

TABLE 3

Mutagenic primers for the construction of streptavidin mutants. Mutated codons are bolded and underlined. Restriction enzymes in brackets behind the mutants refer to the set of enzymes used for cloning.

V125R, V125T (ScaI/SphI)

Forward primer: SAVV125RTF
  5' GGAAAAGTACTCTTA$\underline{C}$/GAGGACATGATAC
  ATTTAC 3'
  (SEQ ID NO: 4)
Backward primer: pUB18H3
  5' GATTTCATACACGGTGCCTG 3'
  (SEQ ID NO: 5)

V55R, V55T (XbaI/SphI)

Forward primer: SAVV55RTF
  5' GAATCTAGATACA$\underline{C}$/GACTTACAGGAAGAT
  ATG 3'
  (SEQ ID NO: 6)
Backward primer: pUB18H3

T76R (BamHI/SphI)

Forward primer: SAVT76RF
  5' GTGGATCCGGAACAGCACTTGGATGGAGAG
  TT 3'
  (SEQ ID NO: 7)
Backward primer:
pUB18H3

D61A W120K (XbaI/ScaI)

Forward primer: SAVD61AF
  5' CATCTAGATACGTGCTTACAGGAAGATAT**G
  CA**TCTGCACCT 3'
  (SEQ ID NO: 8)
Backward primer: SAVW120KB
  5' CAAGAGTACTTTTTTTTGCATTTGC
  TTC 3'
  (SEQ ID NO: 9)

T76R L109T (BamHI/ScaI)

Forward primer: SAVT76RF
Backward primer: SAVL109TB
  5' GAGAGTACTTTTCCATGCATTTGCTTCTGT
  TGTTCCAGATGTTAATGTCCATTGTGTG 3'
  (SEQ ID NO: 10)

Example 2

Production and Purification of Streptavidin

Wild-type streptavidin was produced by *B. subtilis* WB800 [pSSAV-Tcry] cultured in a defined medium (Wu, 2002). The secreted protein was purified to homogeneity using cation exchange followed by iminobiotin affinity chromatography (Qureshi, 2001). Production and purification of streptavidin muteins followed a similar scheme with two major modifications: super-rich medium (Halling, 1977) was used in place of the defined medium and biotin-agarose (Sigma) was used in place of iminobiotin agarose as the affinity matrix. Dialyzed sample containing partially purified mutein was loaded to a 1-ml biotin-agarose column. Streptavidin muteins were eluted from the column using 20 mM d-biotin in phosphate-buffered saline (PBS; 50 mM sodium phosphate, 100 mM NaCl, pH 7.2). Concentration of purified streptavidin was determined spectrophotometrically using the known extinction coefficient at 280 nm (Gill, 1989; Gasteiger, 2003) for each individual mutein.

Example 3

Determination of the Molecular Size of Streptavidin

Molecular mass of purified streptavidin and its muteins was estimated by both gel filtration and dynamic light scattering studies. Gel filtration was performed on the Bio-Rad biologic workstation equipped with a Bio-Prep SE 100/17 column that had been calibrated with molecular mass protein markers (Bio-Rad). Molecular mass was also estimated from the hydrodynamic radius of the mutein obtained using a DynaPro MS dynamic light scattering instrument (Protein Solutions, USA) that had been calibrated with lysozyme. Protein samples (2-3 mg/ml in PBS) were passed through a 0.02 µm filter (Whatman Anodisc 13) immediately prior to measurement. The size distribution profile was analyzed using the manufacturer's Dynamics V6 software.

Figure 3:
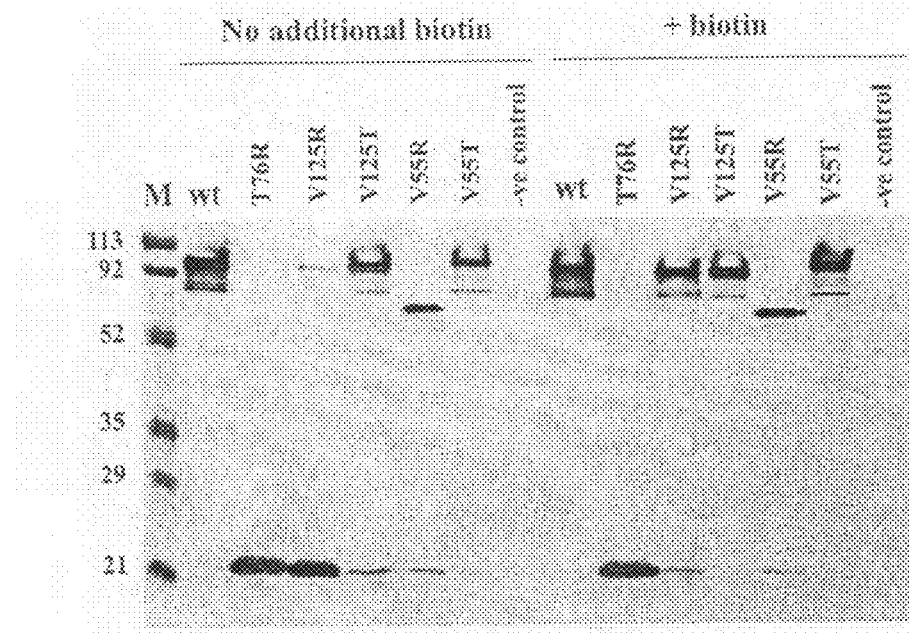
FIG. 3: Western blot analysis of cell culture supernatants from *B. subtilis* strains producing streptavidin muteins carrying a single mutation. 15 μl of non-boiled sample of culture supernatant was loaded to each lane. Samples on the left set were collected from *B. subtilis* strains cultured in super-rich medium without additional supplement of biotin. Samples on the right set were collected from *B. subtilis* strains cultured in super-rich medium with additional supplementation of biotin (20 μM). The blot was probed with polyclonal antibodies against streptavidin and developed using 4-chloro-1-napthol (Bio-Rad) as the colour development agent. Culture supernatant from WB800 [pWB705HM] (Wong et al., 1995), which did not produce any streptavidin served as the negative control. M, molecular weight markers; wt, wild type streptavidin.

In single mutation muteins, the impact of the mutation on weakening of the subunit interaction followed the order T76R>V125R>V125T≈V55R>V55T (FIG. 3 and Table 4). The T76R mutein (referred to herein as M1) existed 100% in the monomeric state on the SDS-polyacrylamide gel even in the presence of biotin. In contrast, V55T mutation had the lowest impact, with the majority of molecules in the tetrameric state even in the absence of added biotin. Presence of biotin shifts the majority of the three remaining muteins (V125R, V125T and V55R) to the tetrameric state. Changing valine to arginine exerted greater impact than changing it to threonine. This is true for both Val-125 and Val-55.

Analysis of the solvent accessibility of individual amino acid residues with tetrameric streptavidin indicates that the solvent accessible area of Thr-76 in subunit A is zero. Its close distances to both Thr-76 and Arg-59 in subunit B and location on a rigid surface of a β-barrel structure make it an ideal residue to be changed to arginine to achieve the maximal electrostatic repulsion and steric hindrance effects at the subunit interface (FIG. 2B). The surface accessible area of Val-125 in subunit A is 1.78%. It has extensive interactions with Leu-109, Trp-120, Thr-123 and Val-125 in subunit D (FIG. 2C), Leu-109 in subunit B and Gln-107 in subunit C. Its conversion to arginine results in charge repulsion in subunit D and potential steric hindrance for subunits B, C, and D. As for Val-55 in subunit A, its surface accessible area is 29.7% and it is only close to Arg-59 in subunit B at the interface (FIG. 2D). Thus, V55R has the least impact on monomerization.

TABLE 4

Summary of the mutagenic effects on weakening of subunit interactions in streptavidin muteins as reflected by the degree of monomerization of streptavidin muteins in SDS-PAGE. Estimation of the percentage of streptavidin in monomeric and tetrameric states (number in the table) is based on the blots showing migration pattern of non-boiled samples in FIG. 3 and 4.

| Streptavidin mutein | No additional biotin | | With additional biotin | |
|---|---|---|---|---|
| | Monomer | Tetramer | Monomer | Tetramer |
| M1 (T76R) | 100 | 0 | 100 | 0 |
| V125R | 92 | 8 | 12 | 88 |
| V125T | 25 | 75 | 0 | 100 |
| V55R | 20 | 80 | 10 | 90 |
| V55T | 1 | 99 | 0 | 100 |
| M2 (T76R, V125R) | 100 | 0 | 100 | 0 |
| M4 (T76R, V125R, V55T, L109T) | 100 | 0 | 100 | 0 |
| AK | 100 | 0 | 100 | 0 |

Figure 6:
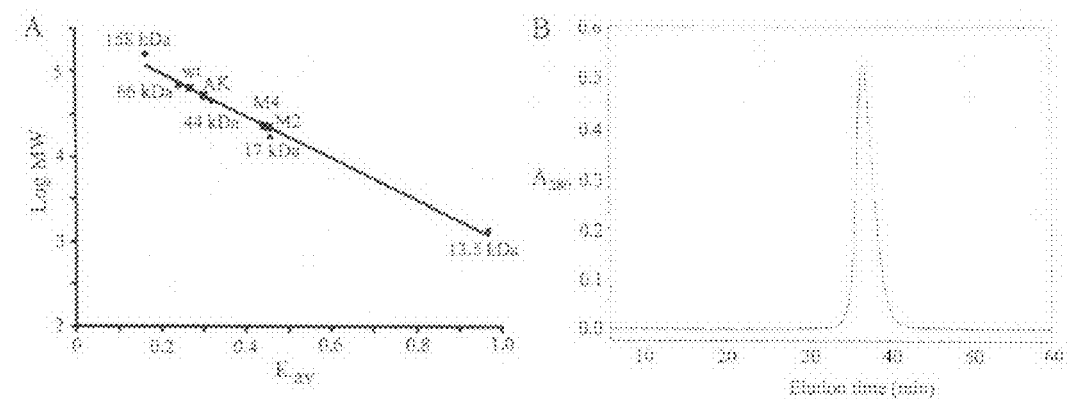
FIG. 6: Gel filtration profiles of streptavidin muteins.

Observation of 100% monomerization of the streptavidin mutein using a non-boiled sample in SDS-PAGE does not always truly reflect its existence in the monomeric state in solution since SDS can promote subunit dissociation (Bayer, 1996; Waner, 2004). The apparent molecular masses of the purified wild-type streptavidin and the three muteins (M2, M4, AK) were estimated by gel filtration (FIG. 6A and Table 5). The expected molecular mass of monomeric streptavidin is 16.5 kDa. M2 and M4 in the absence of biotin showed the apparent molecular mass of 19.95 kDa and 21.87 kDa, respectively. These masses increased slightly in the presence of biotin. These data suggest that the muteins are monomeric in nature since their masses are less than that for the streptavidin dimer (33 kDa). In contrast, the AK mutein showed an apparent molecular mass of 45.66 kDa even in the absence of biotin. This indicates the oligomeric nature of this mutein. FIG. 6B shows the elution profile of purified M4 (in the absence of biotin) from the gel filtration column. The sample (loaded at 2 mg per ml) was eluted as a single peak. There is no evidence for the presence of tetrameric streptavidin, which would be eluted at 30.5 min.

TABLE 5

Molecular mass determination of wild-type (wt) streptavidin and its muteins by gel filtration and dynamic light scattering. In dynamic light scattering, the estimated molecular mass (M) was calculated from the measured hydrodynamic radius ($R_H$) using a protein calibration curve. The peaks have a polydispersity below 15%. Theoretical molecular mass is estimated from the amino acid composition of the mature protein (Gasteiger, 2003).

| Sample | M (kDa) (Gel filtration) | $R_H$ (nm) (Dynamic light scattering) | M (kDa) (Dynamic light scattering) | M (kDa) (Theoretical) |
|---|---|---|---|---|
| Wt (no biotin) | 56.23 | 3.69 ± 0.19 | 69 | 66.0 (tetramer) |
| AK (no biotin) | 45.66 | 3.20 ± 0.23 | 50 | |
| AK (+biotin) | 50.12 | 3.54 ± 0.38 | 63 | |
| M2 (no biotin) | 19.95 | 1.98 ± 0.24 | 17 | 16.5 (monomer) |
| M2 (+biotin) | 23.44 | 2.09 ± 0.29 | 18 | |
| M4 (no biotin) | 21.87 | 2.08 ± 0.31 | 18.1 | 16.5 (monomer) |
| M4 (+biotin) | 24.54 | 2.20 ± 0.14 | 21.5 | |

Since the apparent molecular mass of wild-type streptavidin in the absence of biotin is 10 kDa less than expected (56 kDa instead of 66 kDa) as determined by gel filtration, dynamic light scattering (Schurr, 1977) was used as a second method to estimate the apparent molecular masses. The apparent molecular mass of wild-type streptavidin obtained in this way (69 kDa) was closer to that expected (66 kDa) (Table 5). The apparent molecular masses for both M2 and M4 in the absence of biotin indicated that they were in the monomeric state. Addition of biotin caused only a slight increase in their apparent molecular masses. The AK mutein again was found to be oligomeric independent of the presence or absence of biotin.

Example 4

Proteinase K Digestion of Streptavidin and its Muteins

Purified streptavidin and its muteins (30 µM monomer) were treated with proteinase K (Invitrogen, 5 µM) for 15 min at 30° C. in 50 mM Tris-HCl containing 5 mM CaCl$_2$, pH 8.0. The reaction was stopped by precipitation with trichloroacetic acid (Ellison, 1995). Boiled samples of precipitated proteins were resolved by reducing SDS-PAGE. The same analysis was performed with streptavidin samples treated with biotin (1 mM final concentration) prior to proteinase K digestion.

Figure 7:
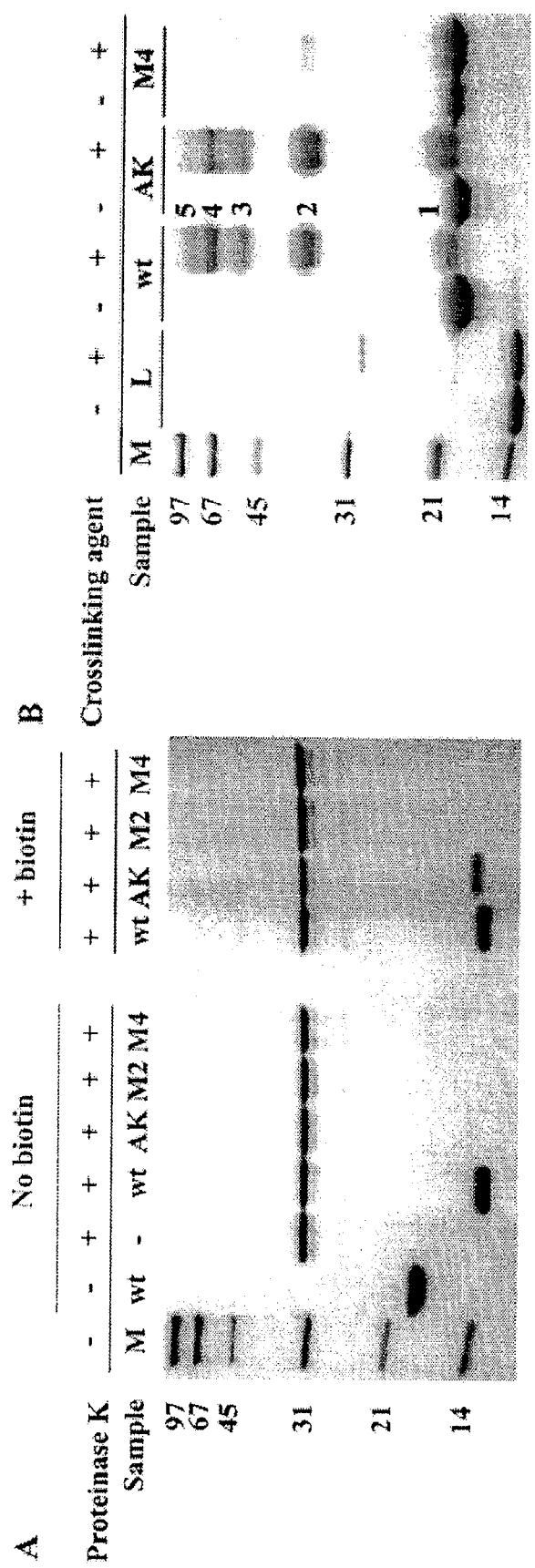
FIG. 7: Determination of the monomeric or oligomeric states of wild-type streptavidin and its muteins. Pictures show the Coomassie blue stained SDS-polyacrylamide gel.

Monomeric streptavidin is expected to be more susceptible to proteinase K digestion (Laitinen, 2003). Therefore, wild type streptavidin and its muteins were treated with proteinase K (FIG. 7A). Wild type streptavidin was converted to the core form independent of the presence or absence of biotin. Under the condition used, the core streptavidin was resistant to further degradation by proteinase K. In contrast, all three muteins including AK, M2 and M4 were much more susceptible to proteinase K digestion. Sensitivity to proteinase K is more apparent for M2 and M4, which were completely digested independent of the presence or absence of biotin. This property is consistent with the monomeric nature of these muteins. The AK mutein behaved differently. While most of it was digested by proteinase K in the absence of biotin, it became much more resistant to proteinase K when biotin was present.

Example 5

Cross-Linking Reactions

Cross-linking of streptavidin and its muteins was carried out using sulfo-EGS [ethylene glycolbis(sulfosuccinimidyl succinate)] (Pierce) as the cross-linker. A typical reaction mixture (20 µl) contained the purified mutein (0.25 mg/ml) and sulfo-EGS (10-fold molar excess over the protein) in PBS. After 30 min at room temperature, the reaction was quenched with Tris-HCl (30 mM, pH 7.5). Aliquots of the cross-linking reaction samples were boiled and examined by SDS-PAGE. Lysozyme (Sigma, 0.25 mg/ml) was included in the study to help establish the optimal reaction conditions.

To strengthen the idea that both M2 and M4 are monomeric while AK is oligomeric in nature, protein cross-linking was carried out using sulfo-EGS as the cross-linking agent. Sulfo-EGS reacts with both the accessible α-amino groups at the N-termini and the surface exposed ε-amino groups of the lysine side-chains in proteins. Secreted wild type streptavidin has eight lysine residues in each subunit. Three dimensional structural model of streptavidin suggests that lysine-121 in subunit A is 14.1 Å from lysine-121 in subunit D. As the spacer arm in sulfo-EGS is 16.1 Å, subunits A and D (same for subunits B and C) should be easily cross-linked by sulfo-EGS. Also, it is possible to have cross-linking between subunits A and B as the N-terminal region from subunit A which contains two lysine residues is likely to be positioned close to lysine-80 in subunit B. The same is true for subunits C and D. Therefore, one should be able to differentiate tetrameric streptavidin from the monomeric form with the observation of cross-linked tetrameric streptavidin using sulfo-EGS. Lysozyme, well known to be monomeric in solution (Blake, 1965; Schwalbe, 2001), served as the negative control. FIG. 7B shows that the amount of dimeric lysozyme increased slightly in the presence of the cross-linking agent. This helped set the upper limit of the concentration of sulfo-EGS to be used under the experimental condition. The wild type streptavidin subunit had an apparent molecular mass of 19 kDa on the SDS-gel. After treatment with sulfo-EGS, most of these subunits were cross-linked to dimers and higher oligomers with small amounts remaining in the monomeric state. M2 and M4 muteins behaved very similarly (data for M2 are not shown). The majority of the M2 and M4 muteins after the cross-linking treatment migrated as monomers with small amounts in the dimeric form. These dimers may represent cross-linked monomeric subunits, which were artificially generated in the same manner as with lysozyme. AK showed a cross-linking profile very similar to that of the wild type streptavidin. These data strongly support the idea that M2 and M4 muteins are monomeric while the AK mutein is oligomeric in solution, respectively.

Example 6

Kinetic Analysis of Streptavidin Muteins

The kinetic parameters (both on- and off-rates for interaction with biotin) of streptavidin muteins were determined in real time using the surface plasmon resonance based BIAcoreX biosensor. Biotin-conjugated bovine serum albumin immobilized on CM5 sensor chip was used to study the reversibility of biotin binding (Qureshi, 2001).

Figure 8:
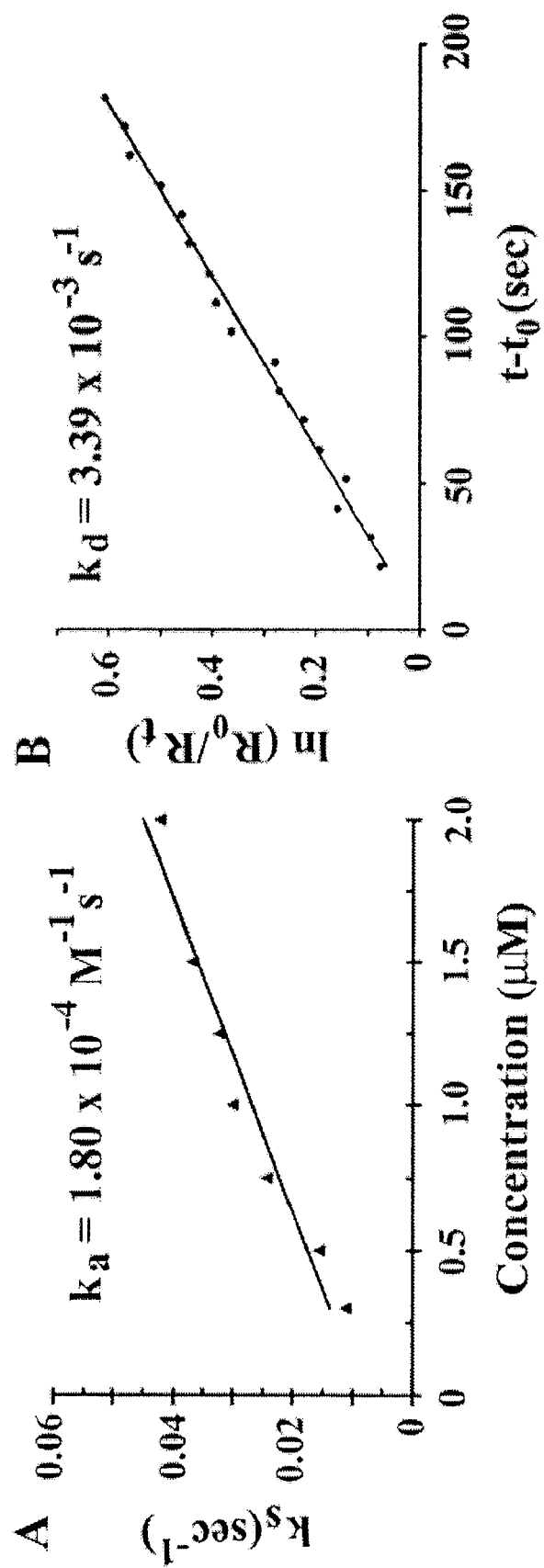
FIG. 8: Kinetic parameters for the interaction between M4 streptavidin mutein and biotin as monitored by BIAcore biosensor. A. On-rate ($k_a$) determination. $k_a$ is derived from association analysis. $k_d$ is the slope of the plot of $\ln(R_o/R_t)$ versus $(t-t_o)$ where $R_o$ is the response at an arbitrary starting time $t_o$; $R_t$ is the response at time t.

As shown in Table 6 (graphical plots for M4 are shown in FIG. 8), M2, M4 and AK had their dissociation constant ($K_d$) in the range of $10^{-7}$M. The off-rates ($k_d$) for these muteins were almost the same while the on-rate ($k_a$) for the AK mutein was slightly lower than the rest. One of the factors affecting on-rate is the diffusion coefficient (or molecular mass) of the streptavidin molecule. Since AK is oligomeric in nature, this may account for the lower on-rate for this mutein-biotin interaction.

TABLE 6

Kinetic parameters for the interactions between streptavidin muteins and biotin.

| Protein | $k_a$ (M$^{-1}$s$^{-1}$) | $k_d$ (s$^{-1}$) | $K_d$ (M) |
|---------|--------------------------|-------------------|-----------|
| M2 | $1.88 \pm 0.07 \times 10^4$ | $3.22 \pm 0.01 \times 10^{-3}$ | $1.71 \pm 0.07 \times 10^{-7}$ |
| M4 | $1.80 \pm 0.04 \times 10^4$ | $3.39 \pm 0.02 \times 10^{-3}$ | $1.87 \pm 0.06 \times 10^{-7}$ |
| AK | $1.46 \pm 0.05 \times 10^4$ | $3.59 \pm 0.03 \times 10^{-3}$ | $2.46 \pm 0.10 \times 10^{-7}$ |

$k_a$, on-rate;
$k_d$, off-rate;
$K_d = k_d/k_a$.

Example 7

Computer Programs for Analyses of Streptavidin

Swiss-pdb Viewer (Guex, 1997) was used to display streptavidin (1SWE (20)), analyze interfacial residues, measure distance between residues and align the structures of streptavidin and avidin. Interfacial contact areas were calculated using the protein-protein interaction server (Jones, 1995) and the Formiga module in the Sting Millennium Suite (Neshich, 2003). The plots of accessible surface area of individual residues in streptavidin in either the monomeric or tetrameric state were generated using the Protein Dossier module in the Sting Millennium Suite.

Example 8

Construction of pET-SAVM4

Plasmid pET-SAVM4 is an expression vector for producing the monomeric streptavidin mutein M4 from *E. coli* using the T7 promoter system. The streptavidin gene bearing 4 mutations was amplified by PCR with the *B. subtilis* plasmid p(T76R, V125R, V55T, L109T) (Bashir, 2001) as the template and synthetic oligonucleotides ECSAVF (5'TGGAC-CCGAGCAAAGATTCTAAAG 3' SEQ ID NO:10) and ECSAVB (5' CTGTCGACTGACTGCGTTAGCAATT- TAAC 3' SEQ ID NO:11) as the forward and backward primers, respectively. The 714-bp amplified product was phosphorylated by T4 polynucleotide kinase and digested with SalI. It was then inserted in-frame to pET29b (Novagen) which has been digested with NdeI (followed by a fill-in reaction to generate a blunt end) and SalI. The resulting plasmid, designated pET-SAVM4, was transformed to E. coli BL21(DE3) (Novagen) for expression studies.

Example 9

Cell Growth

E. coli BL21(DE3)[pET-SAVM4] was grown at 37° C. in Luria broth (1% tryptone, 0.5% yeast extract, 1% NaCl) containing 30 μg/ml kanamycin to 150-200 Klett units in a shake flask. IPTG was then added to a final concentration of 0.1 mM and growth continued for 4-5 hours at 26-28° C. Cell density was measured using a Klett-Summerson photoelectric colorimeter with a green filter (Klett Mfg. Co; New York).

Example 10

Purification of Monomeric Streptavidin

Cells of E. coli BL21(DE3)[pET-SAVM4] were harvested by centrifugation at 12,000 g for 5 min at 4° C. The cell pellet was resuspended in buffer (30 mM Tris-HCl, pH 7.4, 100 mM NaCl, 5 mM EDTA, 1 mM phenylmethylsulfonyl fluoride) and disrupted with a French press. The crude cell lysate was separated into soluble and insoluble fractions by centrifugation at 20,000 g for 20 min. The soluble fraction was dialysed overnight against phosphate-buffered saline (PBS; 50 mM sodium phosphate, 100 mM NaCl, pH 7.2) to remove any biotin contaminants. Monomeric streptavidin in the dialysate was purified on a biotin-agarose column (Sigma) (Wu, 2005). Concentration of purified streptavidin was determined spectrophotometrically at 280 nm using a molar extinction coefficient of 41,820 $M^{-1}cm^{-1}$ for calculation (Gill, 1989).

Example 11

Preparation of Immobilized Monomeric Streptavidin

Pure monomeric M4 streptavidin mutein was used to prepare affinity matrix for the purification of biotinylated proteins. The mutein was coupled to cyanogen-bromide activated agarose (Sigma) according to the manufacturer's instructions. The amount of non-immobilized streptavidin was estimated by colorimetric method using a protein assay reagent (Bio-Rad). The coupling efficiency was determined to be around 70%.

Example 12

Affinity Purification of Biotinylated Proteins

The purification of two biotinylated proteins from a crude sample was used to demonstrate the functionality of the M4 affinity matrix. One protein was chemically biotinylated horse heart cytochrome c (5.5 moles biotin/mole cytochrome c, Sigma); the other was enzymatically biotinylated maltose binding protein-AviTag fusion (MBP-AviTag; 1 mole biotin/mol protein, Avidity). Each protein was mixed with a crude B. subtilis cellular extract that had been pretreated to remove endogenous biotin and biotinylated proteins (Qureshi, 2002). The sample was applied to a 200:1-column of M4 affinity matrix which had been equilibrated in PBS. After washing the matrix with 4-5 column volumes of PBS, the bound proteins were eluted with 10 mM biotin in PBS. The fractions collected were analyzed by SDS-polyacrylamide gel electrophoresis (SDS-PAGE) and, for biotinylated cytochrome c, also by spectrophotometric measurement at 550 nm for the ∀-peak of the reduced heme c moiety of cytochrome c. Regeneration of M4 column and determination of the full binding capacity of the affinity matrix followed the method in an earlier study (Qureshi, 2002).

Example 13

Other Methods

Vent DNA polymerase (New England BioLabs) was used for DNA amplification. The sequence of the PCR product was confirmed to be free of amplification errors by nucleotide sequencing performed at the University Core DNA and protein services, University of Calgary, Calgary, Alberta, Canada. Molecular mass of M4 was determined by SELDI-TOF mass spectrometry on an NP20 chip using sinapic acid as the matrix. The chip array was analyzed in a PBS (Protein Biosystem) II ProteinChip Reader (Ciphergen Biosystems) as described in a previous article (Wu, 2005). The kinetic parameters for monomeric streptavidin to interact with biotinylated bovine serum albumin (BSA) were determined using BIAcore X biosensor as previously described (Qureshi, 2002).

REFERENCES

The following references are referred in parenthesis in the above description and are incorporated herein as if reproduced in their entirety.

Atwell, S., Ultsch, M., De Vos, A. M., and Wells, J. A. (1997) Science 278, 1125-1128

Bashir, R., Gomez, R., Sarikaya, A., Ladisch, M. R., Sturgis, J., and Robinson, J. P. (2001) Adsorption of avidin on microfabricated surfaces for protein biochip applications. Biotechnol. Bioeng. 73, 324-328.

Bayer, E. A., and Wilchek, M. (1990) Application of avidin-biotin technology to affinity based separations. J. Chromatography. 510, 3-11.

Bayer, E. A., Ehrlichrogozinski, S., and Wilchek, M., (1996) Sodium dodecyl sulfate polyacrylamide gel electrophoretic method for assessing the quaternary state and comparative thermostability of avidin and streptavidin. Electrophoresis. 17, 1319-1324.

Bayer, E. A., Ben Hur, H., and Wilchek, M., Isolation and properties of streptavidin, Methods Enzymol. 184:80-9 (1990) 80-89.

Blake, C. C., Koenig, D. F., Mair, G. A., North, A. C., Phillips, D. C., and Sarma, V. R. (1965) Nature 206, 757-761

Casalini, P., Luison, E., Menard, S., Colnaghi, M. I., Paganelli, G., and Canevari, S. (1997) Tumor pretargeting: role of avidin/streptavidin on monoclonal antibody internalisation. J. Nucl. Med. 38, 1378-1381.

Dieckman, L., Gu, M., Stols, L., Donnelly, M. I., and Collart, F. R. (2002) High throughput methods for gene cloning and expression. Protein Expr. Purif. 25, 1-7.

Ellison, D., Hinton, J., Hubbard, S. J., and Beynon, R. J. (1995) Protein Sci. 4, 1337-1345

Freitag, S., Le Trong, I., Chilkoti, A., Klumb, L. A., Stayton, P. S., and Stankamp, R. E. (1998) Structural studies of binding site tryptophan mutants in the high-affinity streptavidin-biotin complex. J. Mol. Biol. 279, 211-221.

Freitag, S., Le Trong, I., Chilkoti, A., Klumb, L. A., Stayton, P. S., and Stenkamp, R. E., Structural studies of binding site tryptophan mutants in the high-affinity streptavidin-biotin complex, J. Mol. Biol. 279 (1998) 211-221.

Gallizia, A., de Lalla, C., Nardone, E., Santambrogio, P., Brandazza, A., Sidoli, A., and Arosio, P., Production of a soluble and functional recombinant streptavidin in *Escherichia coli*, Protein Expr. Purif. 14 (1998) 192-196.

Gasteiger, E., Gattiker, A., Hoogland, C., Ivanyi, I., Appel, R. D., and Bairoch, A. (2003) *Nucleic Acids Res.* 31, 3784-3788

Gill, S. C. and Von Hippel, P. H., (1989) Calculation of protein extinction coefficients from amino acid sequence data, Anal. Biochem. 182, 319-326.

Gonzalez, M., Argarana, C. E., and Fidelio, G. D. (1999) *Biomol. Eng* 16, 67-72

Green, N. M. (1990) Avidin and streptavidin. Methods Enzymol. 184, 51-67.

Guex, N. and Peitsch, M. C. (1997) *Electrophoresis* 18, 2714-2723

Halling, S. M., Sanchez-Anzaldo, F. J., Fukuda, R., Doi, R. H., and Meares, C. F. (1977) *Biochemistry* 16, 2880-2884

Hendrickson, W. A., Pahler, A., Smith, J. L., Satow, Y., Merritt, E. A., and Phizackerley, R. P., (1989) Crystal structure of core streptavidin determined from multi-wavelength anomalous diffraction of synchrotron radiation. Proc. Natl. Acad. Sci. U.S.A. 86, 2190-2194.

Henrikson, K. P., Allen, S. H., and Maloy, W. L., (1979) An avidin monomer affinity column for the purification of biotin-containing enzymes. Anal. Biochem. 94, 366-370.

Hunt, I., (2005) From gene to protein: a review of new and enabling technologies for multi-parallel protein expression. Protein Expr. Purif. 40, 1-22.

Hyre, D. E., Le, Trong, I, Freitag, S., Stenkamp, R. E., and Stayton, P. S., Ser45 plays an important role in managing both the equilibrium and transition state energetics of the streptavidin-biotin system, Protein Sci. 9 (2000) 878-885.

Jones, S, and Thornton, J. M. (1995) Protein-protein interactions: a review of protein dimer structures. Prog. Biophys. Mol. Biol. 63, 31-65.

Kohanski, R. A., and Lane, M. D., (1990) Monovalent avidin affinity columns. Methods Enzymol. 184, 194-200.

Laitinen, O. H., Marttila, A. T., Airenne, K. J., Kulik, T., Livnah, O., Bayer, E. A., Wilchek, M., and Kulomaa, M. S. (2001) Biotin induces tetramerization of a recombinant monomeric avidin. A model for protein-protein interactions. J. Biol. Chem. 276, 8219-8224.

Laitinen, O. H., Nordlund, H. R., Hytonen, V. P., Uotila, S. T., Marttila, A. T., Savolainen, J., Airenne, K. J., Livnah, O., Bayer, E. A., Wilchek, M., and Kulomaa, M. S. (2003) Rational design of an active avidin monomer. J. Biol. Chem. 278, 4010-4014.

Lesley, S. A. (2001) High-throughput proteomics: protein expression and purification in the postgenomic world. Protein Expr. Purif. 22, 159-164.

Lichty, J. J., Malecki, J. L., Angew, H. D., Michelson-Horowitz, D. J., and Tan, S., (2005) Comparison of affinity tag for protein purification. Protein Expr. Purif., 41, 98-105.

Liu, Q., Li, M. Z., Leibham, D., Cortez, D., and Elledge, S. J. (1998) The univector plasmid-fusion system, a method for rapid construction of recombinant DNA without restriction enzymes. Curr. Biol. 8, 1300-1309.

Livnah, O., Bayer, E. A., Wilchek, M., and Sussman, J. L. (1993) Three-dimensional structures of avidin and avidin-biotin complex. Proc. Natl. Acad. Sci. U.S.A. 90, 5076-5080.

Marttila, A. T., Airenne, K. J., Laitinen, O. H., Kulik, T., Bayer, E. A., Wilchek, M., and Kulomaa, M. S. (1998) *FEBS Lett.* 441, 313-317

Marttila, A. T., Laitinen, O. H., Airenne, K. J., Kulik, T., Bayer, E. A., Wilchek, M., and Kulomaa, M. S. (2000) FEBS Lett. 467, 31-36

Neshich, G., Togawa, R. C., Mancini, A. L., Kuser, P. R., Yamagishi, M. E., Pappas, G., Jr., Torres, W. V., Fonseca e Campos, Ferreira, L. L., Luna, F. M., Oliveira, A. G., Miura, R. T., Inoue, M. K., Horita, L. G., de Souza, D. F., Dominiquini, F., Alvaro, A., Lima, C. S., Ogawa, F. O., Gomes, G. B., Palandrani, J. F., dos Santos, G. F., de Freitas, E. M., Mattiuz, A. R., Costa, I. C., de Almeida, C. L., Souza, S., Baudet, C., and Higa, R. H. (2003) *Nucleic Acids Res.* 31, 3386-3392

Niemeyer, C. M., Adler, M., Pignataro, B., Lenhert, S., Gao, S., Chi, L., Fuchs, H., and Blohm, D. (1999) Self-assembly of DNA-streptavidin nanostructures and their use as reagents in immuno-PCR. Nucleic Acids Res. 27, 4553-3451.

Pahler, A., Hendrickson, W. A., Kolks, M. A., Argarana, C. E., and Cantor, C. R., Characterization and crystallization of core streptavidin, J. Biol. Chem. 262 (1987) 13933-13937.

Qureshi, M. H., Yeung, J. C., Wu, S.-C. and Wong, S.-L. (2001) Development and characterization of a series of soluble tetrameric and monomeric streptavidin muteins with differential biotin binding affinities. J. Biol. Chem. 276, 46422-46428.

Qureshi, M. H. and Wong, S.-L., (2002) Design, production and characterization of a monomeric streptavidin and its application for affinity purification of biotinylated proteins. Protein Expr. Purif. 25, 409-415.

Sano, T. and Cantor, C. R. (1995) Intersubunit contacts made by trytophan 120 with biotin are essential for both strong biotin binding and biotin-induced tighter subunit association of streptavidin. Proc. Natl. Acad. Sci. U.S.A. 92, 3180-3184.

Sano, T., Pandori, M. W., Chen, X. M., Smith, C. L., Cantor, C. R., and Chen, X., Recombinant core streptavidins—A minimum-sized core streptavidin has enhanced structural stability and higher accessibility to biotinylated macromolecules, J. Biol. Chem. 270 (1995) 28204-28209.

Schechter, B., Chen, L., Amon, R., and Wilchek, M., (1999) Organ selective delivery using a tissue-directed streptavidin-biotin system: targeting 5-fluorouridine via TNP-streptavidin. J. Drug Target. 6, 337-348.

Scholle, M. D., Collart, F. R., and Kay, B. K. (2004) In vivo biotinylated proteins as targets for phage-display selection experiments. Protein Expr. Purif. 37, 243-252.

Schurr, J. M. (1977) *CRC Crit. Rev. Biochem.* 4, 371-431

Schwalbe, H., Grimshaw, S. B., Spencer, A., Buck, M., Boyd, J., Dobson, C. M., Redfield, C., and Smith, L. J. (2001) *Protein Sci.* 10, 677-688

Sorensen, H. P., Sperling-Petersen, H. U., and Mortensen, K. K., A favorable solubility partner for the recombinant expression of streptavidin, Protein Expr. Purif. 32 (2003) 252-259.

Swint-Kruse, L., Elam, C. R., Lin, J. W., Wycuff, D. R., and Shive, M. K. (2001) *Protein Sci.* 10, 262-276

Szafranski, P., Mello, C. M., Sano, T., Smith, C. L., Kaplan, D. L., and Cantor, C. R., A new approach for containment of microorganisms: dual control of streptavidin expression by antisense RNA and the T7 transcription system, Proc. Natl. Acad. Sci. U.S. A 94 (1997) 1059-1063.

Terpe, K., (2003) Overview of tag protein fusions: from molecular and biochemical fundamentals to commercial systems. Appl. Microbiol. Biotechnol. 60, 523-533.

Vetter, I. R., Baase, W. A., Heinz, D. W., Xiong, J. P., Snow, S., and Matthews, B. W. (1996) *Protein Sci.* 5, 2399-2415

Waner, M. J., Navrotskaya, I., Bain, A., Oldham, E. D., and Mascotti, D. P., (2004) Thermal and sodium dodecylsulfate induced transitions of streptavidin. Biophys. J. 87, 2701-2713.

Weber, P. C., Ohlendorf, D. H., Wendoloski, J. J. and Salemme, F. R. (1989) Structural origins of high-affinity biotin binding to streptavidin. Science. 243, 85-88.

Wilchek, M. and Bayer, E. A. (1988) The avidin-biotin complex in bioanalytical applications. Anal. Biochem. 171, 1-32.

Wilchek, M. and Bayer, E. A. (1990) Introduction to avidin-biotin technology. Methods Enzyymol. 184, 5-13.

Wong, S.-L., X.-C. Wu, L.-P. Yang, S.-C. Ng, and N. Hudson. 1995. Production and purification of antibody using *Bacillus subtilis* as an expression host, p. 100-107. In H. Y. Wang and T. Imanaka (eds.), Antibody Expression and Engineering. American Chemical Society, Washington, D.C.)

Wu, S.-C. and Wong, S.-L. (2005) Engineering soluble monomeric streptavidin with reversible biotin binding capability. J. Biol. Chem. 280, 23225-23231.

Wu, S.-C., Qureshi, M. H., and Wong, S.-L. (2002) *Protein Expr. Purif.*: 24, 348-356

---

What is claimed is:

1. A method of isolating a biotinylated molecule from a sample comprising the steps of binding a streptavidin mutein to a solid support to form a matrix, passing the sample over the support, and eluting the biotinylated molecule, wherein the streptavidin mutein comprises an amino acid sequence having Thr76 of SEQ ID NO:1 substituted with a charged amino acid.

2. The method of claim 1, comprising the further step of regenerating the matrix for reuse.

3. The method of claim 1, wherein said mutein further comprises at least one mutation of a hydrophobic interfacial amino acid residue to a less hydrophobic, charged or hydrophilic residue.

4. The method of claim 3, wherein at least one mutation is selected from the group consisting of:
   a) Val125 of SEQ ID NO:1 substituted with a charged or hydrophilic amino acid;
   b) Val55 of SEQ ID NO:1 substituted with a charged or hydrophilic amino acid; and
   c) Leu109 of SEQ ID NO:1 substituted with a charged or hydrophilic amino acid.

5. The method of claim 1, wherein Thr76 of SEQ ID NO:1 is substituted with Arg, Lys or His.

6. The method of claim 5, wherein Thr76 of SEQ ID NO:1 is substituted with Arg.

7. The method of claim 5, wherein Thr76 of SEQ ID NO:1 is substituted with Lys.

8. The method of claim 5, wherein Thr76 of SEQ ID NO:1 is substituted with His.

9. The method of claim 4, wherein Val125 of SEQ ID NO:1 is substituted with Arg, Lys or His.

10. The method of claim 9, wherein Val125 of SEQ ID NO:1 is substituted with Arg.

11. The method of claim 4, wherein Val55 of SEQ ID NO:1 is substituted with Thr or Ser.

12. The method of claim 11, wherein Val55 of SEQ ID NO:1 is substituted with Thr.

13. The method of claim 4, wherein Leu109 of SEQ ID NO: 1 is substituted with Thr or Ser.

14. The method of claim 13, wherein Leu109 of SEQ ID NO:1 is substituted with Thr.

15. The method of claim 4, wherein said mutein further comprises at least four mutations where Thr76 of SEQ ID NO:1 is substituted with Arg, Val125 is substituted with Arg, Val55 is substituted with Thr; and Leu109 is substituted with Thr.

16. The method of claim 1, wherein said mutein exists in monomeric form in solution in the presence of biotin.

17. The method of claim 1, wherein the mutation is chosen to cause one or more of steric hindrance, charge repulsion, and improvement of solubility by changing interfacial hydrophobic residues to less hydrophobic or hydrophilic ones.

* * * * *

SEQUENCE LISTING

```
<160> NUMBER OF SEQ ID NOS: 19

<210> SEQ ID NO 1
<211> LENGTH: 159
<212> TYPE: PRT
<213> ORGANISM: Streptomyces sp.

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 638
<212> TYPE: DNA
<213> ORGANISM: Streptomyces sp.

<400> SEQUENCE: 2
ccctccgtcc ccgccgggca acaactaggg agtattttc gtgtctcaca tgcgcaagat        60
cgtcgttgca gccatcgccg tttccctgac cacggtctcg attacggcca gcgcttcggc       120
agacccctcc aaggactcga aggcccaggt ctcggccgcc gaggccggca tcaccggcac       180
ctggtacaac cagctcggct cgaccttcat cgtgaccgcg ggcgccgacg gcgccctgac       240
cggaacctac gagtcggccg tcggcaacgc cgagagccgc tacgtcctga ccggtcgtta       300
cgacagcgcc ccggccaccg acggcagcgg caccgccctc ggttggacgg tggcctggaa       360
gaataactac cgcaacgccc actccgcgac cacgtggagc ggccagtacg tcggcggcgc       420
```

```
cgaggcgagg atcaacaccc agtggctgct gacctccggc accaccgagg ccaacgcctg    480
gaagtccacg ctggtcggcc acgacacctt caccaaggtg aagccgtccg ccgcctccat    540
cgacgcggcg aagaaggccg gcgtcaacaa cggcaacccg ctcgacgccg ttcagcagta    600
gtcgcgtccc ggcaccggcg ggtgccggga cctcggcc                            638
```

<210> SEQ ID NO 3
<211> LENGTH: 567
<212> TYPE: DNA
<213> ORGANISM: Artificial
<220> FEATURE:
<223> OTHER INFORMATION: A synthetic streptavidin gene for expression in
      B. subtilis.

<400> SEQUENCE: 3

```
atgaacatca aaagtttgc aaaacaagca acagtattaa cctttactac cgcactgctg    60
gcaggaggcg caactcaagc ttttgcagac ccgagcaaag attctaaagc acaagtatct   120
gctgcagaag caggaattac aggcacatgg tataatcagc tgggatctac atttattgtt   180
acagccggcg cagatggagc tcttacagga acatatgaat ctgctgttgg aaatgcagaa   240
tctagataca cacttacagg aagatatgat tctgcacctg caacagatgg atccggaaca   300
gcacttggat ggagagttgc atggaaaaac aattatagaa acgcacatag cgctacaaca   360
tggtctggcc aatatacagg aggtgcagaa gcaagaatta acacacaatg gacattaaca   420
tctggaacaa cagaagcaaa tgcagataaa agtactacaa gaggacatga tacatttaca   480
aaagttaaac ctagcgcagc atctatcgat gcagcgaaaa agcaggagt taacaatggc   540 aatcctttag atgcagttca acaataa                                       567
```

<210> SEQ ID NO 4
<211> LENGTH: 34
<212> TYPE: DNA
<213> ORGANISM: Artificial
<220> FEATURE:
<223> OTHER INFORMATION: Mutagenic forward primer for constructon of
      streptavidin mutein comprising single point mutation at V125

<400> SEQUENCE: 4

```
ggaaaagtac tcttasagga catgatacat ttac                                34
```

<210> SEQ ID NO 5
<211> LENGTH: 20
<212> TYPE: DNA
<213> ORGANISM: Artificial
<220> FEATURE:
<223> OTHER INFORMATION: Mutagenic backward primer for construction of
      streptavidin mutein comprising single point mutation at V125

<400> SEQUENCE: 5

```
gatttcatac acggtgcctg                                                20
```

<210> SEQ ID NO 6
<211> LENGTH: 31
<212> TYPE: DNA
<213> ORGANISM: Artificial
<220> FEATURE:
<223> OTHER INFORMATION: Mutagenic forward primer for construction of
      streptavidin mutein comprising of single point mutation at V55

<400> SEQUENCE: 6

```
gaatctagat acasacttac aggaagatat g                                   31
```

<210> SEQ ID NO 7
<211> LENGTH: 32
<212> TYPE: DNA
<213> ORGANISM: Artificial
<220> FEATURE:
<223> OTHER INFORMATION: Mutagenic forward primer for construction of
      streptavidin mutein comprising of single point mutation at T76

<400> SEQUENCE: 7
gtggatccgg aacagcactt ggatggagag tt                                32

<210> SEQ ID NO 8
<211> LENGTH: 41
<212> TYPE: DNA
<213> ORGANISM: Artificial
<220> FEATURE:
<223> OTHER INFORMATION: Mutagenic forward primer for construction of
      streptavidin mutein comprising of double point mutation (D61 W120)

<400> SEQUENCE: 8
catctagata cgtgcttaca ggaagatatg catctgcacc t                       41

<210> SEQ ID NO 9
<211> LENGTH: 28
<212> TYPE: DNA
<213> ORGANISM: Artificial
<220> FEATURE:
<223> OTHER INFORMATION: Mutagenic backward primer for construction of
      streptavidin mutein comprising double point mutation (D61 W120)

<400> SEQUENCE: 9
caagagtact tttttttgca tttgcttc                                      28

<210> SEQ ID NO 10
<211> LENGTH: 58
<212> TYPE: DNA
<213> ORGANISM: Artificial
<220> FEATURE:
<223> OTHER INFORMATION: Mutagenic backward primer for construction of
      streptavidin mutein comprising double point mutation (T76 L109)

<400> SEQUENCE: 10
gagagtactt ttccatgcat ttgcttctgt tgttccagat gttaatgtcc attgtgtg     58

<210> SEQ ID NO 11
<211> LENGTH: 24
<212> TYPE: DNA
<213> ORGANISM: Artificial
<220> FEATURE:
<223> OTHER INFORMATION: Synthetic oligonucleotide forward primer for
      PCR amplification of streptavidin gene bearing four mutations

<400> SEQUENCE: 11
tggacccgag caaagattct aaag                                          24

<210> SEQ ID NO 12
<211> LENGTH: 29
<212> TYPE: DNA
<213> ORGANISM: Artificial
<220> FEATURE:
<223> OTHER INFORMATION: Synthetic oligonucleotide backward primer for
      PCT amplification of streptavidin gene bearing four mutations

<400> SEQUENCE: 12
ctgtcgactg actgcgttag caatttaac                                     29

<210> SEQ ID NO 13
<211> LENGTH: 188
<212> TYPE: PRT
<213> ORGANISM: Artificial
<220> FEATURE:
<223> OTHER INFORMATION: Protein sequence for the streptavidin precursor
     (wild type, full length) for the production in B. subtilis

<400> SEQUENCE: 13

Met Asn Ile Lys Lys Phe Ala Lys Gln Ala Thr Val Leu Thr Phe Thr
1               5                  10                  15

Thr Ala Leu Leu Ala Gly Gly Ala Thr Gln Ala Phe Ala Asp Pro Ser
            20                  25                  30

Lys Asp Ser Lys Ala Gln Val Ser Ala Ala Glu Ala Gly Ile Thr Gly
        35                  40                  45

Thr Trp Tyr Asn Gln Leu Gly Ser Thr Phe Ile Val Thr Ala Gly Ala
    50                  55                  60

Asp Gly Ala Leu Thr Gly Thr Tyr Glu Ser Ala Val Gly Asn Ala Glu
65                  70                  75                  80

Ser Arg Tyr Thr Leu Thr Gly Arg Tyr Asp Ser Ala Pro Ala Thr Asp
                85                  90                  95

Gly Ser Gly Thr Ala Leu Gly Trp Arg Val Ala Trp Lys Asn Asn Tyr
            100                 105                 110

Arg Asn Ala His Ser Ala Thr Thr Trp Ser Gly Gln Tyr Thr Gly Gly
        115                 120                 125

Ala Glu Ala Arg Ile Asn Thr Gln Trp Thr Leu Thr Ser Gly Thr Thr
    130                 135                 140

Glu Ala Asn Ala Asp Lys Ser Thr Thr Arg Gly His Asp Thr Phe Thr
145                 150                 155                 160

Lys Val Lys Pro Ser Ala Ala Ser Ile Asp Ala Ala Lys Lys Ala Gly
                165                 170                 175

Val Asn Asn Gly Asn Pro Leu Asp Ala Val Gln Gln
            180                 185

<210> SEQ ID NO 14
<211> LENGTH: 567
<212> TYPE: DNA
<213> ORGANISM: Artificial
<220> FEATURE:
<223> OTHER INFORMATION: Coding sequence for secretory production of
     streptavidin M4 in B. subtilis

<400> SEQUENCE: 14
atgaacatca aaaagtttgc aaaacaagca acagtattaa cctttactac cgcactgctg      60
gcaggaggcg caactcaagc ttttgcagac ccgagcaaag attctaaagc acaagtatct     120
gctgcagaag caggaattac aggcacatgg tataatcagc tgggatctac atttattgtt     180
acagccggcg cagatggagc tcttacagga acatatgaat ctgctgttgg aaatgcagaa     240
tctagataca cacttacagg aagatatgat tctgcacctg caacagatgg atccggaaca     300
gcacttggat ggagagttgc atggaaaaac aattatagaa acgcacatag cgctacaaca     360
tggtctggcc aatatgtggg aggtgcagaa gcaagaatta cacacaatg gacattaaca     420 tctggaacaa cagaagcaaa tgcatggaaa agtactctta gaggacatga tacatttaca     480
aaagttaaac ctagcgcagc atctatcgat gcagcgaaaa agcaggagt taacaatggc     540 aatcctttag atgcagttca acaataa                                         567

<210> SEQ ID NO 15

<211> LENGTH: 188
<212> TYPE: PRT
<213> ORGANISM: Artificial
<220> FEATURE:
<223> OTHER INFORMATION: Amino acid sequence for secretory production of streptavidin M4 in b. subtilis

<400> SEQUENCE: 15

```
Met Asn Ile Lys Lys Phe Ala Lys Gln Ala Thr Val Leu Thr Phe Thr
1               5                   10                  15
Thr Ala Leu Leu Ala Gly Gly Ala Thr Gln Ala Phe Ala Asp Pro Ser
                20                  25                  30
Lys Asp Ser Lys Ala Gln Val Ser Ala Ala Glu Ala Gly Ile Thr Gly
            35                  40                  45
Thr Trp Tyr Asn Gln Leu Gly Ser Thr Phe Ile Val Thr Ala Gly Ala
        50                  55                  60
Asp Gly Ala Leu Thr Gly Thr Tyr Glu Ser Ala Val Gly Asn Ala Glu
65                  70                  75                  80
Ser Arg Tyr Thr Leu Thr Gly Arg Tyr Asp Ser Ala Pro Ala Thr Asp
                85                  90                  95
Gly Ser Gly Thr Ala Leu Gly Trp Arg Val Ala Trp Lys Asn Asn Tyr
            100                 105                 110
Arg Asn Ala His Ser Ala Thr Thr Trp Ser Gly Gln Tyr Val Gly Gly
        115                 120                 125
Ala Glu Ala Arg Ile Asn Thr Gln Trp Thr Leu Thr Ser Gly Thr Thr
    130                 135                 140
Glu Ala Asn Ala Trp Lys Ser Thr Leu Arg Gly His Asp Thr Phe Thr
145                 150                 155                 160
Lys Val Lys Pro Ser Ala Ser Ile Asp Ala Ala Lys Lys Ala Gly
                165                 170                 175
Val Asn Asn Gly Asn Pro Leu Asp Ala Val Gln Gln
            180                 185
```

<210> SEQ ID NO 16
<211> LENGTH: 4792
<212> TYPE: DNA
<213> ORGANISM: Artificial
<220> FEATURE:
<223> OTHER INFORMATION: Artificial primer

<400> SEQUENCE: 16

```
gaattcgagc tcagcattat tgagtggatg attatattcc ttttgatagg tggtatgttt      60
tcgcttgaac ttttaaatac agccattgaa catacggttg atttaataac tgacaaacat     120
caccctcttg ctaaagcggc caaggacgct gccgccgggg ctgtttgcgt ttttgccgtg     180
atttcgtgta tcattggttt acttattttt ttgccaaagc tgtaatggct gaaaattctt     240
acatttattt tacattttta gaaatgggcg tgaaaaaaag cgcgcgatta tgtaaaatat     300
aaagtgatag cggtaccagg aggggcggaa gaagcagacc gctaacacag tacataaaaa     360
aggagacatg aacgatgaac atcaaaaagt ttgcaaaaca agcaacagta ttaacccttta    420
ctaccgcact gctggcagga ggcgcaactc aagcttttgc agacccgagc aaagattcta    480
aagcacaagt atctgctgca gaagcaggaa ttacaggcac atggtataat cagctgggat    540
ctacatttat tgttacagcc ggcgcagatg gagctcttac aggaacatat gaatctgctg    600
ttggaaatgc agaatctaga tacacactta caggaagata tgattctgca cctgcaacag    660
atggatccgg aacagcactt ggatggagag ttgcatggaa aacaattat agaaacgcac     720
```

```
atagcgctac aacatggtct ggccaatatg tgggaggtgc agaagcaaga attaacacac      780
aatggacatt aacatctgga acaacagaag caaatgcatg gaaaagtact cttagaggac      840
atgatacatt tacaaaagtt aaacctagcg cagcatctat cgatgcagcg aaaaaagcag      900
gagttaacaa tggcaatcct ttagatgcag ttcaacaata atgatcagat atctagtctc      960
atgcaaactc aggtttaaat atcgttttca aatcaattgt ccaagagcag cattacaaat     1020
agataagtaa tttgttgtaa tgaaaaacgg acatcacctc cattgaaacg gagtgatgtc     1080
cgttttacta tgttattttc tagtaatacg catgcaagct agctttaatg cggtagttta     1140
tcacagttaa attgctaacg cagtcaggca ccgtgtatga atctaacaa tgcgctcatc      1200
gtcatcctcg gcaccgtcac cctggatgct gtaggcatag gcttggttat gccggtactg     1260
ccgggcctct tgcgggatct gattcactt tttgcattct acaaactgca taactctat       1320
gtaaatcgct ccttttagg tggcacaaat gtgaggcatt ttcgctcttt ccggcaacca      1380
cttccaagta aagtataaca cactatactt tatattcata aagtgtgtgc tctgcgaggc     1440
tgtcggcagt gccgaccaaa accataaaac ctttaagacc tttcttttt ttacgagaaa      1500
aaagaaacaa aaaaacctgc cctctgccac ctcagcaaag gggggttttg ctctcgtgct     1560
cgtttaaaaa tcagcaaggg acaggtagta ttttttgaga agatcactca aaaaatctcc     1620
acctttaaac ccttgccaat ttttatttg tccgttttgt ctagcttacc gaaagccaga      1680
ctcagcaaga ataaaatttt tattgtcttt cggttttcta gtgtaacgga caaaaccact     1740
caaaataaaa aagatacaag agaggtctct cgtatctttt attcagcaat cgcgcccgat     1800
tgctgaacag attaataata gattttagct ttttatttgt tgaaaaaagc taatcaaatt     1860
gttgtcggga tcaattactg caaagtctcg ttcatcccac cactgatctt ttaatgatgt     1920
attggggtgc aaaatgccca aaggcttaat atgttgatat aattcatcaa ttccctctac     1980
ttcaatgcgg caactagcag taccagcaat aaacgactcc gcacctgtac aaaccggtga     2040
atcattacta cgagagcgcc agccttcatc acttgcctcc catagatgaa tccgaacctc     2100
attacacatt agaactgcga atccatcttc atggtgaacc aaagtgaaac ctagtttatc     2160
gcaataaaaa cctatactct ttttaatatc cccgactggc aatgccggga tagactgtaa     2220
cattctcacg cataaaatcc cctttcattt tctaatgtaa atctattacc ttattattaa     2280
ttcaattcgc tcataattaa tcctttttct tattacgcaa aatggcccga tttaagcaca     2340
cccttttattc cgttaatgcg ccatgacagc catgataatt actaatacta ggagaagtta    2400
ataaatacgt aaccaacatg attaacaatt attagaggtc atcgttcaaa atggtatgcg     2460
ttttgacaca tccactatat atccgtgtcg ttctgtccac tcctgaatcc cattccagaa     2520
attctctagc gattccagaa gtttctcaga gtcggaaagt tgaccagaca ttacgaactg     2580
gcacagatgg tcataacctg aaggaagatc tgattgctta actgcttcag ttaagaccga     2640
agcgctcgtc gtataacaga tgcgatgatg cagaccaatc aacatggcac ctgccattgc     2700
tacctgtaca gtcaaggatg gtagaaatgt tgtcggtcct tgcacacgaa tattacgcca     2760
tttgcctgca tattcaaaca gctcttctac gataagggca caaatcgcat cgtggaacgt     2820
ttgggcttct accgatttag cagtttgata cactttctct aagtatccac ctgaatcata     2880
aatcggcaaa atagagaaaa attgaccatg tgtaagcggc caatctgatt ccacctgaga     2940
tgcataatct agtagaatct cttcgctatc aaaattcact tccaccttcc actcaccggt     3000
tgtccattca tggctgaact ctgcttcctc tgttgacatg acacacatca tctcaatatc     3060
cgaatagggc ccatcagtct gacgaccaag agagccataa acaccaatag ccttaacatc     3120
```

| | |
|---|---|
| atccccatat ttatccaata ttcgttcctt aatttcatga acaatcttca ttctttcttc | 3180 |
| tctagtcatt attattggtc cattcactat tctcattccc ttttcagata tgcttttcta | 3240 |
| aataagaata tttggagagc accgttctta ttcagctatt cttcctaagc atccttcaat | 3300 |
| ccttttaata acaattatag catctaatct ggcccgtttg ttgaactact ctttaataaa | 3360 |
| ataattttc cgttcccaat aataatagaa atccatctt catcggcttt tcgtcatca | 3420 |
| tctgtatgaa ttcttctgtg tcatcaaggt ttaatttttt atgtatttct tttaacaaac | 3480 |
| gattaacctt ttacggtgta aaccttcctc caaatcagac aaacgtttca ttcatcatcg | 3540 |
| gtcataaaat ccgtatcctt tacaggatat tttgcagttt attttagatt aataactcgt | 3600 |
| tcaacaaact tccacattgc tcaaatcgcc caccatagga aattcttttc cgtcaattgc | 3660 |
| cgattgtata tccgatttat atttattttt cggtcgaatc atttgaactt ttacatttgg | 3720 |
| atcatagtct aatttcattg cctttttcca aaattgaatc cattgttttt gattcacgta | 3780 |
| gttttctgta ttcttaaaat aagttggttc cacacatacc aatacatgca tgtgctgatt | 3840 |
| ataagaatta tctttattat ttattgtcac ttccgttgca cgcataaaac caacaagatt | 3900 |
| tttattaatt ttttatatt gcatcattcg gcgaaatcct tgagccatat ctgacaaact | 3960 |
| cttatttaat tcttcgccat cataaacatt tttaactgtt aatgtgagaa caaccaacg | 4020 |
| aactgttggc ttttgtttaa taacttcagc aacaaccttt tgtgactgaa tgccatgttt | 4080 |
| cattgctctc ctccagttgc acattggaca aagcctggat ttacaaaacc acactcgata | 4140 |
| caactttctt tcgcctgttt cacgattttg tttatactct aatatttcag cacaatcttt | 4200 |
| tactctttca gccttttaa attcaagaat atgcagaagt tcaaagtaat caacattagc | 4260 |
| gattttcttt tctctccatg gtctcacttt tccacttttt gtcttgtcca ctaaaaccct | 4320 |
| tgatttttca tctgaataaa tgctactatt aggacacata atattaaaag aaaccccat | 4380 |
| ctatttagtt atttgtttag tcacttataa ctttaacaga tggggttttt ctgtgcaacc | 4440 |
| aattttaagg gttttcaata ctttaaaaca catacatacc aacacttcaa cgcaccttc | 4500 |
| agcaactaaa ataaaatga cgttatttct atatgtatca agataagaaa gaacaagttc | 4560 |
| aaaaccatca aaaaagaca cctttcagg tgcttttttt attttataaa ctcattccct | 4620 |
| gatctcgact tcgttctttt tttacctctc ggttatgagt tagttcaaat tcgttctttt | 4680 |
| taggttctaa atcgtgtttt tcttggaatt gtgctgtttt atcctttacc ttgtctacaa | 4740 |
| accccttaaa aacgttttta aaggctttta agccgtctgt acgttcctta ag | 4792 |

<210> SEQ ID NO 17
<211> LENGTH: 5967
<212> TYPE: DNA
<213> ORGANISM: Artificial
<220> FEATURE:
<223> OTHER INFORMATION: Artificial primer

<400> SEQUENCE: 17

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |

```
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta       540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa ataaggttat caagtgaga       780 aatcaccatg agtgacgact gaatccggtg agaatggcaa agtttatgc atttctttcc       840 agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg caacgctac      1200 ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt tctgcgcgt aatctgctgc ttgcaaacaa aaaaaccacc gctaccagcg      1560
gtggtttgtt tgccggatca agagctacca actcttttc cgaaggtaac tggcttcagc      1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata gtcgtgtct taccggggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga      1920 aaggcggaca ggtatccggt aagcggcagg gtcggaacag gagagcgcac gagggagctt     1980 ccaggggaa acgcctggta tctttatagt cctgtcgggt ttcgccacct ctgacttgag      2040
cgtcgatttt tgtgatgctc gtcagggggg cggagcctat ggaaaaacgc cagcaacgcg     2100 gccttttac ggttcctggc cttttgctgg cttttgctc acatgttctt tcctgcgtta       2160 tccctgatt ctgtggataa ccgtattacc gcctttgagt gagctgatac cgctcgccgc      2220
agccgaacga ccgagcgcag cgagtcagtg agcgaggaag cggaagagcg cctgatgcgg     2280 tatttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac accgctgac gcgccctgac gggcttgtct      2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
```

```
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtcccgga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcga tctcgatccc    4980
gcgaaattaa tacgactcac tatagggaa ttgtgagcgg ataacaattc ccctctagaa    5040
ataattttgt ttaactttaa gaaggagata tacatatgga cccgagcaaa gattctaaag    5100
```

-continued

```
cacaagtatc tgctgcagaa gcaggaatta caggcacatg gtataatcag ctgggatcta   5160
catttattgt tacagccggc gcagatggag ctcttacagg aacatatgaa tctgctgttg   5220
gaaatgcaga atctagatac acacttacag gaagatatga ttctgcacct gcaacagatg   5280
gatccggaac agcacttgga tggagagttg catggaaaaa caattataga aacgcacata   5340
gcgctacaac atggtctggc caatatgtgg gaggtgcaga agcaagaatt aacacacaat   5400
ggacattaac atctggaaca acagaagcaa atgcatggaa aagtactctt agaggacatg   5460
atacatttac aaaagttaaa cctagcgcag catctatcga tgcagcgaaa aaagcaggag   5520
ttaacaatgg caatccttta gatgcagttc aacaataatg atcagatatc tagtctcatg   5580
caaactcagg tttaaatatc gttttcaaat caattgtcca agagcagcat tacaaataga   5640
taagtaattt gttgtaatga aaacggaca tcacctccat tgaaacggag tgatgtccgt     5700
tttactatgt tattttctag taatacgcat gcaagctagc tttaatgcgg tagtttatca   5760
cagttaaatt gctaacgcag tcagtcgaca agcttgcggc cgcactcgag caccaccacc   5820
accaccactg agatccggct gctaacaaag cccgaaagga agctgagttg gctgctgcca   5880
ccgctgagca ataactagca taaccccttg gggcctctaa acgggtcttg agggggttttt   5940 tgctgaaagg aggaactata tccggat                                        5967
```

<210> SEQ ID NO 18
<211> LENGTH: 483
<212> TYPE: PRT
<213> ORGANISM: Artificial
<220> FEATURE:
<223> OTHER INFORMATION: Artificial peptide

<400> SEQUENCE: 18

```
Ala Thr Gly Gly Ala Cys Cys Cys Gly Ala Gly Cys Ala Ala Gly
  1               5                  10                  15

Ala Thr Thr Cys Thr Ala Ala Ala Gly Cys Ala Cys Ala Ala Gly Thr
                 20                  25                  30

Ala Thr Cys Thr Gly Cys Thr Gly Cys Ala Gly Ala Ala Gly Cys Ala
             35                  40                  45

Gly Gly Ala Ala Thr Thr Ala Cys Ala Gly Gly Cys Ala Cys Ala Thr
         50                  55                  60

Gly Gly Thr Ala Thr Ala Ala Thr Cys Ala Gly Cys Thr Gly Gly Gly
 65                  70                  75                  80

Ala Thr Cys Thr Ala Cys Ala Thr Thr Thr Ala Thr Thr Gly Thr Thr
                 85                  90                  95

Ala Cys Ala Gly Cys Cys Gly Gly Cys Gly Cys Ala Gly Ala Thr Gly
                100                 105                 110

Gly Ala Gly Cys Thr Cys Thr Thr Ala Cys Ala Gly Gly Ala Ala Cys
            115                 120                 125

Ala Thr Ala Thr Gly Ala Ala Thr Cys Thr Gly Cys Thr Gly Thr Thr
         130                 135                 140

Gly Gly Ala Ala Ala Thr Gly Cys Ala Gly Ala Ala Thr Cys Thr Ala
145                 150                 155                 160

Gly Ala Thr Ala Cys Ala Cys Ala Cys Thr Thr Ala Cys Ala Gly Gly
                165                 170                 175

Ala Ala Gly Ala Thr Ala Thr Gly Ala Thr Thr Cys Thr Gly Cys Ala
                180                 185                 190

Cys Cys Thr Gly Cys Ala Ala Cys Ala Gly Ala Thr Gly Gly Ala Thr
            195                 200                 205
```

Cys Cys Gly Gly Ala Ala Cys Ala Gly Cys Ala Cys Thr Thr Gly Gly
            210                 215                 220

Ala Thr Gly Gly Ala Gly Ala Gly Thr Thr Gly Cys Ala Thr Gly Gly
225                 230                 235                 240

Ala Ala Ala Ala Ala Cys Ala Ala Thr Thr Ala Thr Ala Gly Ala Ala
                    245                 250                 255

Ala Cys Gly Cys Ala Cys Ala Thr Ala Gly Cys Gly Cys Thr Ala Cys
                260                 265                 270

Ala Ala Cys Ala Thr Gly Gly Thr Cys Thr Gly Gly Cys Cys Ala Ala
            275                 280                 285

Thr Ala Thr Gly Thr Gly Gly Ala Gly Gly Thr Gly Cys Ala Gly
        290                 295                 300

Ala Ala Gly Cys Ala Ala Gly Ala Ala Thr Thr Ala Ala Cys Ala Cys
305                 310                 315                 320

Ala Cys Ala Ala Thr Gly Gly Ala Cys Ala Thr Thr Ala Ala Cys Ala
                325                 330                 335

Thr Cys Thr Gly Gly Ala Ala Cys Ala Ala Cys Ala Gly Ala Ala Gly
            340                 345                 350

Cys Ala Ala Ala Thr Gly Cys Ala Thr Gly Gly Ala Ala Ala Ala Gly
            355                 360                 365

Thr Ala Cys Thr Cys Thr Thr Ala Gly Ala Gly Gly Ala Cys Ala Thr
        370                 375                 380

Gly Ala Thr Ala Cys Ala Thr Thr Thr Ala Cys Ala Ala Ala Ala Gly
385                 390                 395                 400

Thr Thr Ala Ala Cys Cys Thr Ala Gly Cys Gly Cys Cys Ala Gly Cys
                    405                 410                 415

Ala Thr Cys Thr Ala Thr Cys Gly Ala Thr Gly Cys Ala Gly Cys Gly
                420                 425                 430

Ala Ala Ala Ala Ala Gly Cys Ala Gly Gly Ala Gly Thr Thr Ala
            435                 440                 445

Ala Cys Ala Ala Thr Gly Gly Cys Ala Ala Thr Cys Cys Thr Thr Thr
        450                 455                 460

Ala Gly Ala Thr Gly Cys Ala Gly Thr Thr Cys Ala Ala Cys Ala Ala
465                 470                 475                 480

Thr Ala Ala

<210> SEQ ID NO 19
<211> LENGTH: 160
<212> TYPE: PRT
<213> ORGANISM: Artificial
<220> FEATURE:
<223> OTHER INFORMATION: Artificial peptide

<400> SEQUENCE: 19

Met Asp Pro Ser Lys Asp Ser Lys Ala Gln Val Ser Ala Ala Glu Ala
1               5                   10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Thr Leu Thr Gly Arg Tyr Asp Ser Ala
    50                  55                  60

Pro Ala Thr Asp Gly Ser Gly Thr Ala Leu Gly Trp Arg Val Ala Trp
65                  70                  75                  80

Lys Asn Asn Tyr Arg Asn Ala His Ser Ala Thr Thr Trp Ser Gly Gln

-continued

```
                    85                  90                  95
Tyr Val Gly Gly Ala Glu Ala Arg Ile Asn Thr Gln Trp Thr Leu Thr
            100                 105                 110

Ser Gly Thr Thr Glu Ala Asn Ala Trp Lys Ser Thr Leu Arg Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160
```